(12) United States Patent
Shenvi et al.

(10) Patent No.: US 8,642,766 B2
(45) Date of Patent: Feb. 4, 2014

(54) SYNTHESIS OF (+) CORTISTATIN A AND RELATED COMPOUNDS

(76) Inventors: Ryan A. Shenvi, San Diego, CA (US); Carlos A. Guerrero, San Diego, CA (US); Jun Shi, San Diego, CA (US); Chuang-Chuang Li, San Diego, CA (US); Phil S. Baran, San Diego, CA (US)

( * ) Notice: Subject to any disclaimer, the term of this patent is extended or adjusted under 35 U.S.C. 154(b) by 142 days.

(21) Appl. No.: 12/991,081

(22) PCT Filed: Apr. 30, 2009

(86) PCT No.: PCT/US2009/042394
§ 371 (c)(1),
(2), (4) Date: Nov. 4, 2010

(87) PCT Pub. No.: WO2009/137335
PCT Pub. Date: Nov. 12, 2009

(65) Prior Publication Data
US 2011/0060140 A1     Mar. 10, 2011

Related U.S. Application Data

(60) Provisional application No. 61/050,434, filed on May 5, 2008.

(51) Int. Cl.
C07D 217/00 (2006.01)
C07D 311/00 (2006.01)

(52) U.S. Cl.
USPC .......................................... 546/139; 549/382

(58) Field of Classification Search
USPC .......................................... 546/139; 549/382
See application file for complete search history.

(56) References Cited

U.S. PATENT DOCUMENTS

2011/0190323 A1* 8/2011 Flyer et al. ............... 514/266.24

OTHER PUBLICATIONS

Lee et al., Enantioselective Synthesis of (+)-Cortistatin A, a Potent and Selective Inhibitor of Endothelial Cell Proliferation, Journal of the American Chemical Society, vol. 130, No. 50, pp. 16864-16866, 2008.*

* cited by examiner

*Primary Examiner* — Brenda Coleman
(74) *Attorney, Agent, or Firm* — Husch Blackwell, LLP

(57) ABSTRACT

An in vitro synthesis of (+) cortistatin A from readily available precursors is disclosed, as are the syntheses of related 17-aryl substituted compounds, the 17-aryl substituted compounds themselves and novel compounds useful in their preparation.

7 Claims, No Drawings

SYNTHESIS OF (+) CORTISTATIN A AND RELATED COMPOUNDS

CROSS-REFERENCE TO RELATED APPLICATION

This application claims priority from provisional application No. 61/050,434, filed May 5, 2008, whose disclosures are incorporated herein by reference.

GOVERNMENTAL SUPPORT

This invention was made with governmental support under Contract No. GM070414 awarded by the National Institutes of Health. The government has certain rights in this invention.

TECHNICAL FIELD

The present invention relates to a natural product called (+)cortistatin A and related compounds that are synthetic analogues of that natural product and methods of preparing the same. More particularly, the invention contemplates the synthesis of (+)cortistatin A and related compounds.

BACKGROUND ART

Seventy-four percent of all anti-cancer drugs produced over the last two decades have found their origin in natural products. Cortistatin A, below, is a marine steroid with highly selective, and

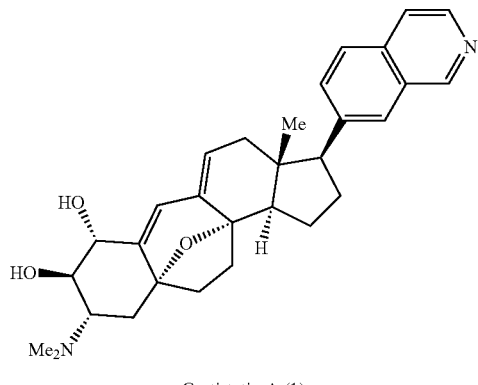

Cortistatin A (1)

perhaps mechanistically unique anti-angiogenic activity. Owing to its remarkable pharmacological potential a number of efforts across the world have been devoted to procuring useful quantities of cortistatin A through chemical synthesis.

Steroids have historically elicited attention from the chemical sciences owing to their utility in living systems, as well as their intrinsic and diverse beauty [C. Djerassi, "Steroids Made it Possible". In *Profiles, Pathways and Dreams*; Seeman, J. I., Ed. (American Chemical Society: Washington, D.C., 1990)]. The cortistatin family (cortistatin A-L;

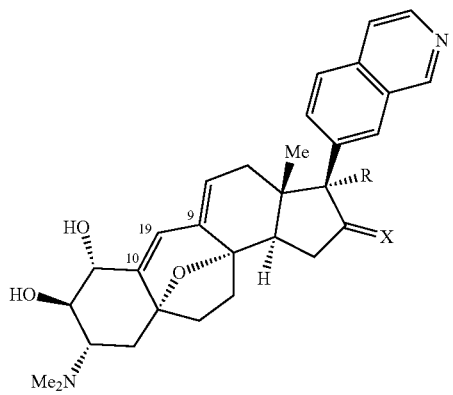

A (1): R = H, X = $H_2$
B (2): R = H, X = α-H, β-OH
C (3): R = H, X = O
D (4): R = OH, X = O

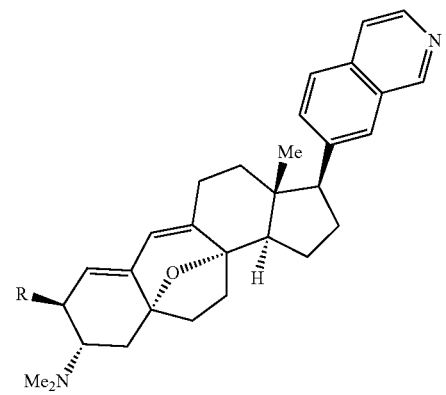

K (6): R = H
L (7): R = OH

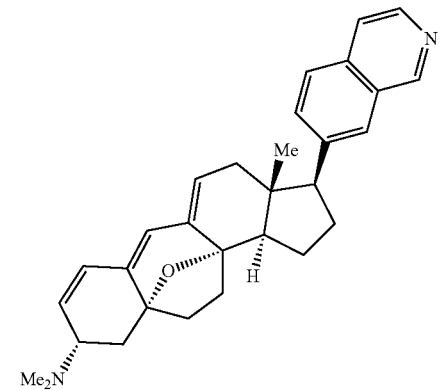

J (5)

above, Compounds 1-7 and others) [Aoki et al., *J. Am. Chem. Soc.* 128, 3148 (2006); Watanabe et al., *Tetrahedron* 63, 4074 (2007); Aoki et al., *Tetrahedron Lett.* 48, 4485 (2007)], a collection of unusual, marine 9(10-19)-abeo-androstane steroids, is certainly no exception: aside from challenging stereochemistry and an odd bricolage of functional groups, the salient feature of these sponge metabolites is, inescapably, their biological activity.

Cortistatin A, the most potent member of the small family, inhibits the proliferation of human umbilical vein endothelial cells (HUVECs, $IC_{50}=1.8$ nM), evidently with no general toxicity toward either healthy or cancerous cell lines ($IC_{50\ (testing\ cells)}/IC_{50\ (HUVECs)} \geq 3300$) [Aoki et al., *J. Am. Chem. Soc.* 128, 3148 (2006)]. From initial pharmacological studies, binding appears to occur reversibly, but to an unknown target, inhibiting the phosphorylation of an unidentified 110 kDa protein, and implying a pathway that may be unique to known anti-angiogenesis compounds [Aoki et al., *Bioorganic & Medicinal Chemistry* 15, 6758 (2007)].

Since the isolation of the first angiogenesis inhibitors [Taylor et al., *Nature* 297, 307 (1982)] and growth factors [Shing et al., *Science* 1984, 223, 1296] in the Folkman laboratories over 25 years ago, pathological angiogenesis has become recognized as an 'organizing principle' for understanding a variety of otherwise disparate disorders [Folkman, *Nature Reviews Drug Discovery* 6, 273 (2007)]. The most familiar application of anti-angiogenesis therapy effects the regression of solid tumors, where inhibitors are responsible for both direct anti-tumor activity [Folkman, in *Holland Frei—Cancer Medicine* 7, D. W. Kufe et al., Eds., (American Association for Cancer Research, B. C. Decker, Hamilton, Ontario, Canada, ed. 7, 2006), pp. 157-191; Folkman, in *Accomplishments in Cancer Research*, Wells et al., Eds. (Lippincott Williams & Wilkins, New York, 1998) pp. 32-44], and increased chemotherapeutic uptake through vascular in the clinic [Satchi-Fainaro et al., *Cancer Cell.* 7, 251 (2005)], prompting further exploration of both terrestrial and marine environments [Aoki et al., *J. Am. Chem. Soc.* 128, 3148 (2006)]. However, access to sufficient quantities of marine macroorganism natural products—the cortistatins, for instance, were isolated from the marine sponge Corticium simplex—is generally impeded by prohibitively expensive isolation work and ecological considerations [Newman et al., *Curr. Med. Chem.* 11, 1693 (2004); Marris, *Nature* 443, 914 (2006)], thus necessitating chemical synthesis.

Compelled by the pharmacological potential of the cortistatins [Aoki et al., *Bioorganic & Medicinal Chemistry* 15, 6758 (2007); Carmeliet, *Nature* 438, 932 (2005)] together with the unanswered questions surrounding their biological activity, we embarked on a synthesis of cortistatin A [C. Djerassi, "Steroids Made it Possible". In *Profiles, Pathways and Dreams*; Seeman, J. I., Ed. (American Chemical Society: Washington, D.C., 1990)], aiming for a concise route from inexpensive, commercially available materials, and the opportunity to develop new chemistry as the occasion arose. Corollary to these goals was our group's ongoing interest in minimizing functional group interconversions (FGIs) [Corey et al., *The Logic of Chemical Synthesis* (Wiley, New York, 1995] through a diminished reliance on protecting groups [Maimone et al., *Nature* 446, 404 (2007)].

The disclosure that follows provides the first synthesis of this natural product and related analogues. This synthesis proceeds by way of 'cortistatinone,' an intermediate ideally suited for investigating the key pharmacophore of the cortistatin family.

BRIEF SUMMARY OF THE INVENTION

The present invention contemplates the preparation of (+)cortistatin I (below),

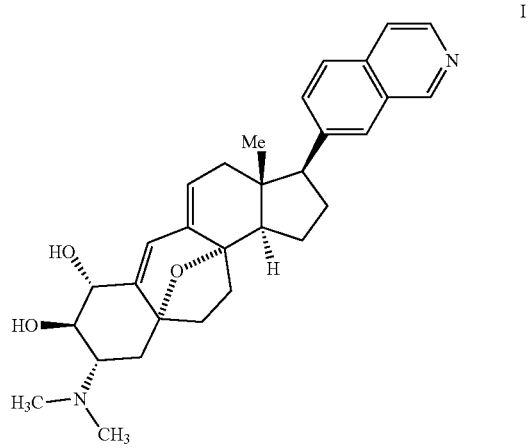

intermediates in its preparation as well as related compounds. Also contemplated are methods of preparing those compounds.

Thus, one embodiment contemplates a compound whose structure corresponds to Formula I

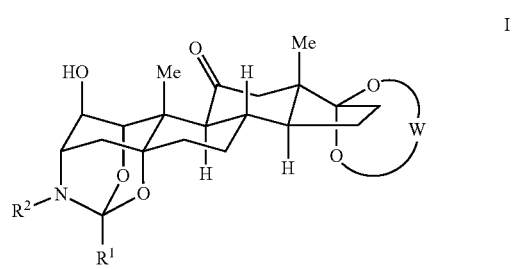

in which W is the residuum of a saturated or unsaturated diol of 2 to about 12 carbon atoms that has been reacted with a ketone group to form the depicted ketal; $R^2$ is COR, $CO_2R$, $SO_2R$, or $P(O)(OR)_2$, where R is hydrido (H), a straight chain, branched chain or cyclic hydrocarbyl (alkyl, alkenyl, or alkynyl) moiety, an aromatic, heterocyclic or alicyclic moiety that contains 1 to about 24 carbon atoms, in which a heterocyclic moiety contains 1 to four rings that each contain up to four ring atoms other than carbon that can be oxygen, nitrogen or sulfur; and $R^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur.

Still another embodiment contemplates a compound whose structure corresponds to Formula V

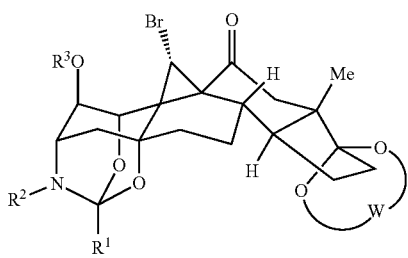

V wherein W, $R^1$ and $R^2$ are defined above, and $R^3$ is a removable $C_1$-$C_{21}$ hydroxyl protecting group.

Yet another embodiment contemplates a compound whose structure corresponds to Formula VI

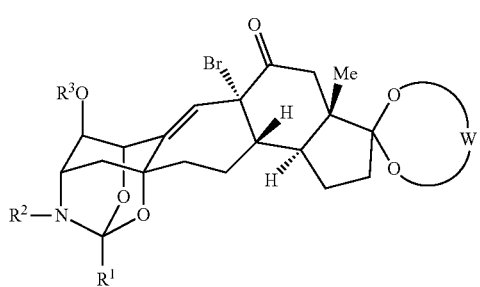

VI wherein W, $R^1$, $R^2$ and $R^3$ are defined above.

Further contemplated is a compound whose structure corresponds to Formula VII

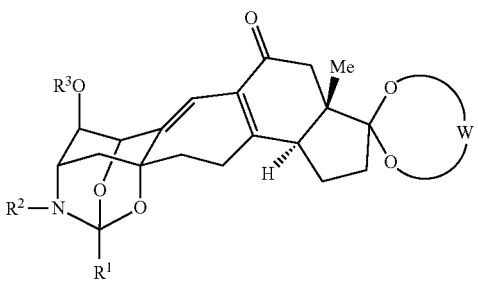

VII wherein W, $R^1$, $R^2$ and $R^3$ are defined above.

Another contemplated embodiment is a compound whose structure corresponds to Formula VIII

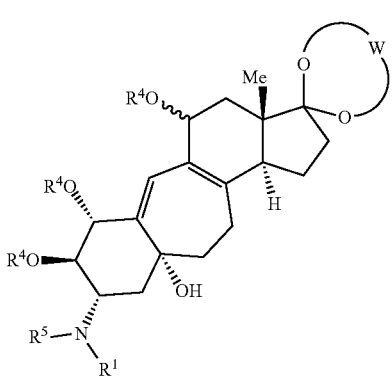

VIII wherein W, and $R^1$ are defined above, $R^4$ is an acyl group COR, $CO_2R$, $SO_2R$, or $P(O)(OR)_2$ that contains 1 to about 24 carbon atoms that can be a $C_1$-$C_{24}$ straight chain, branched chain or cyclic alkyl, alkenyl, or alkynyl moiety, an aromatic, heterocyclic or alicyclic moiety, in which a heterocyclic moiety can contain 1 to four rings that each contain up to four ring atoms other than carbon that can be oxygen, nitrogen or sulfur; and $R^5$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur.

Yet further contemplated is a compound whose structure corresponds to Formula IX,

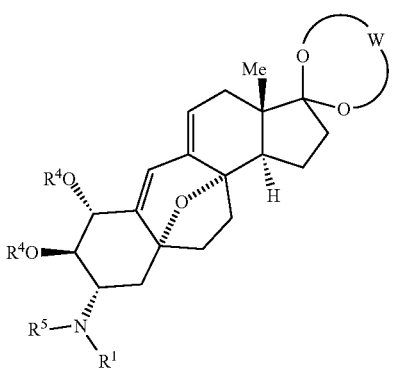

IX wherein W, $R^1$, $R^4$ and $R^5$ are defined above.

Another compound contemplated herein corresponds in structure to Formula X,

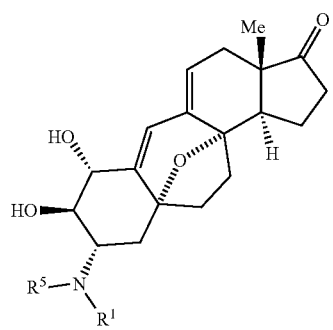

X wherein $R^1$ and $R^5$ are defined above.

A further compound contemplated herein corresponds in structure to Formula XI,

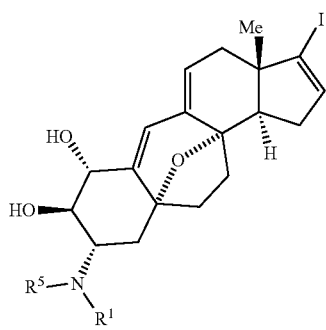

XI wherein $R^1$ and $R^5$ are defined above.

A still further compound contemplated herein corresponds in structure to Formula XII,

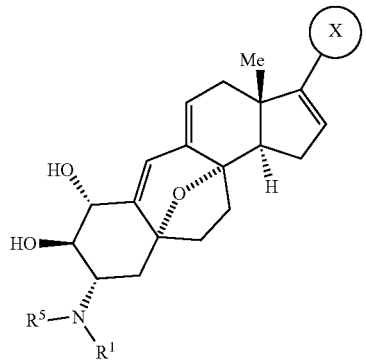

XII wherein $R^1$ and $R^5$ are defined above, and the circled X is a cyclic or heterocyclic substituent that contains 4 to about 15 carbon atoms, contains one to three saturated or unsaturated rings and up to three atoms per ring that are other than carbon and can be oxygen, nitrogen or sulfur. Circled X is preferably an aromatic moiety.

Yet another compound contemplated herein corresponds in structure to Formula XIII,

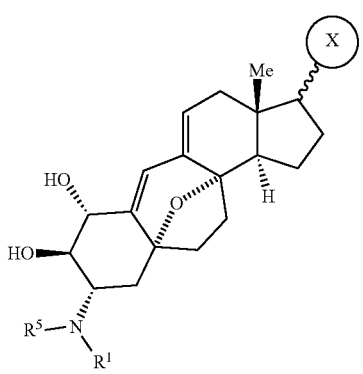

XIII wherein $R^1$ and $R^5$ and the circled X are defined above, and the wavy line indicates that α-, β- and both α- and β-orientations of circled X are contemplated, with the proviso that $R^1$ and $R^5$ are not both methyl when the circled X is a 7-isoquinolinyl. Circled X is preferably aromatic, and is preferably in the β-configuration. In a contemplated synthesis method, $R^1$ and $R^5$ can both be methyl when circled X is 7-isoquinolinyl.

The present invention has several benefits and advantages. Salient among these is that this invention provides the first in vitro synthesis of cortistatin A.

An advantage of this invention is that the synthesis can begin using a readily available starting steroid, prednisone.

Another benefit of the invention is that compounds related to cortistatin A that possess different substituents on the nitrogen atom are readily prepared.

Another advantage of the invention is that compounds related to cortistatin A that possess different D-ring C-17 substituents can be readily prepared.

Yet a further advantage of the invention is that $\Delta^{16}$-cortistatin analogues that exhibit biological activities similar to that of (+)cortistatin A can readily be prepared.

Still further benefits and advantages will be apparent to the skilled worker from the discussion that follows.

DETAILED DESCRIPTION OF THE INVENTION

The synthesis begins with a terrestrial steroid and traverses a route to cortistatin A and related steroidal compounds through the discovery of unique chemical reactivity. By "related steroidal compound" is meant a compound containing at least four fused rings, each containing 5-7 ring atoms, which are arrayed as are the four fused A, B, C and D rings of a steroid.

Specifically, the first example of a directed, geminal C—H bis-oxidation is illustrated in this disclosure; a new fragmentation cascade to access expanded B-ring steroid systems; a chemoselective cyclization to install the hallmark oxabicycle of the cortistatin family; and a remarkably selective hydrogenation reaction, which should find extensive use in future syntheses of the cortistatins and related steroidal compounds. The illustrative synthesis displays a level of brevity, efficiency, and practicality that is useful in evaluating the medicinal potential of this fascinating class of marine steroids.

A crucial target structure became the cortistatin A ketonic core, (+)cortistatinone (Compound 8, below), which was anticipated to permit

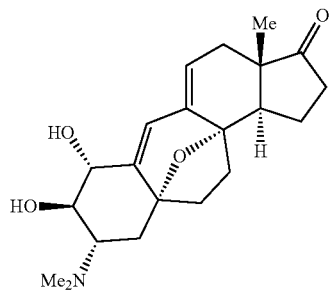

Cortistatinone 8 straight forward elaboration to the natural product, as well as divergence to other family members. Notably, the natural products themselves are so scarce that no authentic sample of cortistatin A could be spared for comparison to synthetic material, without impeding the biological studies already underway.

After careful consideration, a semi-synthetic route to these marine steroids beginning from the abundant terrestrial steroid prednisone was deemed an acceptable strategy for the following reasons: 1) the opportunity to render a semi-synthesis amenable to analogue synthesis, contrary to popular intuition; 2) the occasion to develop new chemical methods and tactics to achieve such ends; and 3) the economy of using prednisone, which at 1.2 $/g possesses 70% of the carbon atoms and the corresponding, enantio-pure chirality of Compound 1. However, numerous problems then stood to be addressed, including control of all 4 A-ring stereocenters, oxidation of the functionally isolated 19- and 8-carbons, C—C-bond-cleaving expansion of the B-ring, and chemo-/stereoselective installation of the isoquinoline side chain. A solution to those problems is described herein, providing access to enantiomerically pure, synthetic cortistatin A (1), with an efficiency useful for extensive pharmacological study.

A contemplated cortistatin compound is preferably synthesized using prednisone [17α,21-dihydroxy-1,4-pregnadiene- 3,11,20-trione], whose structural formula is shown below, or its reduction product, prednisolone, below, whose C-ring hydroxyl would have to be oxidized at some time during the synthesis, as a starting material.

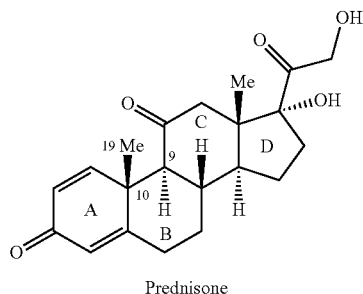

Prednisone

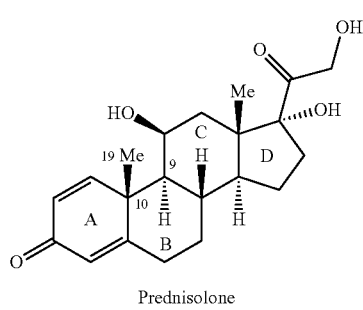

Prednisolone

In carrying out a contemplated synthesis, the prednisone D-ring hydroxyketone group bonded to carbon-17 is cleaved and the D-ring hydroxyl also originally bonded to carbon-17 is oxidized to a ketone. The resulting ketone is protected with a diol to form a ketal compound whose structure corresponds to Formula II,

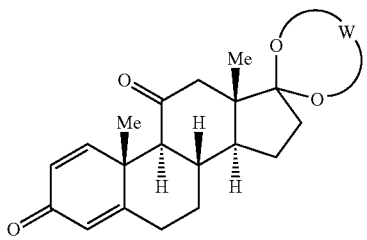

II wherein W is a saturated or unsaturated group of 2 to about 12 carbon atoms that are bonded to the depicted oxygen atoms. W is thus the residuum of a diol that has been reacted with a ketone functionality to form a ketal. Illustrative W diols include ethylene glycol (2 carbon atoms), which is preferred, 1,3-propanediol, propylene glycol, 2,3-butanediol, 2,4-pentanediol, 1,2-cyclohexanediol, cis-exo-2,3-norbornanediol, 2,3-dihydroxynaphthalene, and 2,3-dihydroxyquinoline. It is preferred that the diol and the resulting ketal functionality be symmetric so that diastereomeric or enantiomeric isomers are not formed on formation of the ketal.

The 1,2-double bond of a compound of Formula II is thereafter epoxidized to form the corresponding α-epoxide. Substantially any epoxy-forming reagent can be used for the oxidation reaction, but hydroperoxide compounds such as t-butyl hydroperoxide, benzoyl hydroperoxide, acetic hydroperoxide, trifluoroacetic hydroperoxide and the like are preferred.

The keto group at the 3-position of the resulting diketoepoxide is thereafter converted by reductive amination to an α-amido group by reaction first with an ammonium compound such as ammonium acetate and reduction with a borohydride reagent such as sodium cyanoborohydride or sodium triacetoxyborohydride.

The α-amine so formed is then acylated with a convenient acylating group that can serve as an amine protecting group or as both a protecting group and a precursor for a substituent group ($R^5$) present on the amine of a cortistatin. Illustrative acyl amine protecting groups include those used in peptide synthesis such as t-BOC, f-MOC, and CBZ, as well as methanesulfonyl, benzenesulfonyl, toluenesulfonyl, $C_1$-$C_6$-carbamoyl and di-$C_1$-$C_6$-phosphoryl groups. Illustrative protecting groups can be referred to as COR, $CO_2R$, $SO_2R$, or $P(O)(OR)_2$ groups, where R contains 1 to about 24 carbon atoms. Illustrative protecting/precursor acyl groups can be a $C_1$-$C_{24}$ straight chain, branched chain or cyclic hydrocarbyl (i.e., alkyl, alkenyl, or alkynyl) moiety, an aromatic, heterocyclic or alicyclic moiety, and a heterocyclic moiety can contain 1 to four rings that each contain up to four ring atoms other than carbon that can be oxygen, nitrogen or sulfur. $C_1$-$C_6$ Acyl groups such as formyl, acetyl, propionyl, butyryl, iso-butyryl, pentanoyl and hexanoyl are preferred.

The resulting epoxide compound corresponds in structure to Formula III, below,

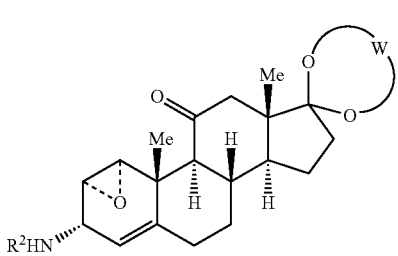

III wherein W is as previously defined, and $R^2$ is COR, $CO_2R$, $SO_2R$, or $P(O)(OR)_2$, where R is a straight chain, branched chain or cyclic hydrocarbyl (alkyl, alkenyl, or alkynyl) moiety, an aromatic, heterocyclic or alicyclic moiety that contains 1 to about 24 carbon atoms, and the heterocyclic moiety contains 1 to four rings that each contain up to four ring atoms other than carbon that can be oxygen, nitrogen or sulfur.

Reaction of a compound of Formula III with a tetrabutyl ammonium $C_1$-$C_6$-carboxylate such as tetrabutyl ammonium acetate (TBAA) in refluxing benzene opens the epoxide at C2, producing the trans-hydroxy acetate, a compound of Formula IV, where W and $R^2$ are as before, and $R^4$ is hydrido or a substituent group that contains up to about 5 carbon atoms such as methyl, ethyl, prop-2-ynyl, cyclopentyl, or 2-furanyl. Benzene can be replaced by toluene or similar solvent, and cobalt (II) acetoacetate is preferably present, as its presence enhances yield, but it is not needed. When used, cobalt (II) acetoacetate is present in a catalytic amount in the reaction medium.

IV

The resulting trisubstituted amido trans-hydroxy acetate (IV) is thereafter hydrated by reaction with molecular oxygen and phenylsilane (or other reductant such as triethylsilane or 2-propanol), preferably in the presence of a catalytic amount of a cobalt or manganese catalysts such as cobalt (II) acetoacetate or cobalt (II) bis(trifluoroacetate), under Mukaiyama hydration conditions followed by reaction of the amidodiol so formed with trimethyl orthoformate. Trimethyl orthoformate can be replaced by another ortho ester such as a tri-$C_1$-$C_6$-alkyl ortho ester of a carboxylic acid having 1 to about 24 carbon atoms of a straight chain, branched chain or cyclic alkyl, alkenyl, or alkynyl moiety, an aromatic, heterocyclic or alicyclic moiety, in which the heterocyclic moiety contains 1 to four rings that each contain up to four ring atoms other than carbon that can be oxygen, nitrogen or sulfur, like trimethoxypentane. Solvolysis of the C2-acetate of the compound so formed provides a compound of Formula I, below.

I wherein
$R_2$ and W are as defined before; and
$R_1$ is hydrido (H), a straight chain, branched chain or cyclic hydrocarbyl (alkyl, alkenyl, or alkynyl) moiety, an aromatic, heterocyclic or alicyclic moiety that contains one to about 24 carbon atoms and the heterocyclic moiety contains 1 to four rings that each contain up to four ring atoms other than carbon that can be oxygen, nitrogen or sulfur.

A compound of Formula I is reacted with in situ-generated acetoxy hypobromite (AcOBr) in a new process conceived to access a dibrominated 19-carbon. Here, phenyliodine(bis) acetate [PhI(OAc)$_2$] is reacted under a non-reactive atmosphere such as argon or nitrogen in dichloromethane or similar solvent such as chloroform with bromine at a temperature of about −30° C. to about −40° C. using a suitable light source (visible and/or UV) such as a sunlamp (75 W, 18 inches above surface of cooling bath) for a time period of about 6 to about 18 hours. Thereafter, the β-hydroxyl group is protected with a suitable, removable $C_1$-$C_{21}$ hydroxyl protecting group such as a formyl group or more preferably a trisubstituted silyl group where the substituents are $C_1$-$C_6$-alkyl, benzyl and phenyl. Illustrative protecting groups include trimethylsilyl, triethylsilyl, dimethylhexylsilyl, diphenylmethylsilyl, triphenylsilyl, tribenzylsilyl, and the like. The protected β-hydroxy-C-19-dibromide is then reacted with a non-nucleophilic strong base such as DBU, DBN, Hunig's base (diisopropyl-ethylamine), 1,8-bis(dimethylamino)naphthalene, a tri-$C_1$-$C_6$-trialkylamine such as triethylamine and lithium chloride or other metal salts in an anhydrous ether solvent such as THF at ambient temperature for about 6 to about 18 hours to form a bromo-cyclopropane product compound of Formula V, below.

V wherein $R^1$, $R^2$ and W are as before, and $R^3$ is a removable $C_1$-$C_{21}$ hydroxyl protecting group such as a removable trisubstituted silyl hydroxyl protecting group.

Reaction of a Compound of Formula V in the presence of an excess of SmI$_2$ with 2,4,4,6-tetrabromo-2,5-cyclohexadienone (TBCHD) produces a compound whose B-ring is (i) opened, (ii) unsaturated and (iii) expanded to seven members that also contains an α-bromoketone, such as a compound of Formula VI, below.

VI wherein $R^1$, $R^2$, $R^3$ and W are as before.

Elimination of the α-bromide from a compound of Formula IV using lithium carbonate provides a cross-conjugated compound of Formula VII, wherein $R^1$, $R^2$, $R^3$ and W are as before.

VII

Reaction of a compound of Formula VII with alane or similar reductant and an acylating agent such as a $C_1$-$C_6$ anhydride like acetic anhydride or an $R^2$ acylating agent reduces the ketone, opens the heteroadamantane core and acylates the resulting hydroxyl to provide a tri-acylated compound of Formula VIII, wherein $R^1$, and W are as before, $R^4$ is an acyl group COR, $CO_2R$, $SO_2R$, or $P(O)(OR)_2$, where R contains 1 to about 24 carbon atoms that can be a $C_1$-$C_{24}$ straight chain, branched chain or cyclic hydrocarbyl (alkyl, alkenyl, or alkynyl) moiety, an aromatic, heterocyclic or alicyclic moiety, in which a heterocyclic moiety can contain 1 to four rings that each contain up to four ring atoms other than carbon that can be oxygen, nitrogen or sulfur, and $R^5$ is hydrido (H), a straight chain, branched chain or cyclic alkyl, alkenyl, or alkynyl moiety, an aromatic, heterocyclic or alicyclic moiety that contains one to about 24 carbon atoms and the heterocyclic moiety contains 1 to four rings that each contain up to four ring atoms other than carbon that can be oxygen, nitrogen or sulfur.

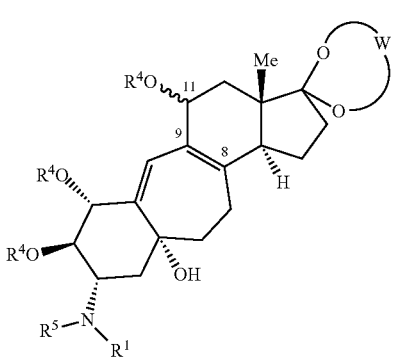

VIII

Reaction of a compound of Formula VIII, a slight molar excess of magnesium bromide and more that a two-fold excess of a non-nucleophilic, relatively weak base such as 2,6-di-(t-butyl)pyridine ($pK_a$ about 3.6) in refluxing benzene forms the ether link, displaces an acylated oxygen at C-11 and rearranges the double bonds to form a compound of Formula IX, wherein $R^1$, $R^4$, $R^5$ and W are as before.

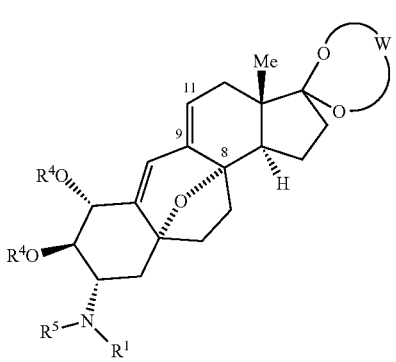

IX

Reaction of a compound of Formula IX with a weak acid such as pyridinium p-toluenesulfonate (PPTS) in water:butanone at elevated temperature to hydrolyze the ketal, followed by neutralization in an excess of a weak base ($pK_a$ about 9) provides a cortistatinone of Formula X in unprotected form, wherein $R^1$ and $R^5$ are as before. When both of $R^1$ and $R^5$ are methyl, a compound of Formula X is (+)cortistatinone (Compound 8).

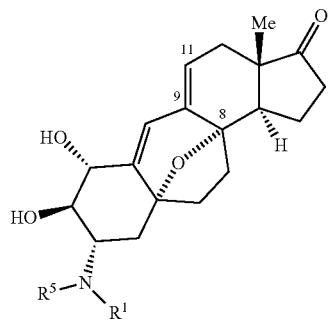

X

Reaction of a compound of Formula X with hydrazine to form the 17-carbon hydrazone followed by reaction with excess iodine and excess tri-$C_1$-$C_6$-alkylamine forms an alkenyl iodide in the D-ring of a compound of Formula XI, in which $R^1$ and $R^5$ are as before defined.

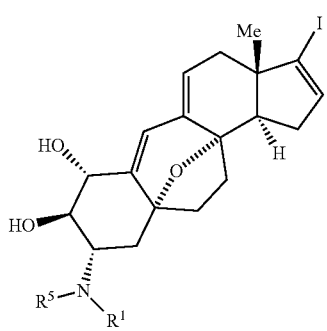

XI

Stille coupling of a compound of Formula XI with an appropriate trimethyltin derivative of a cyclic or heterocyclic compound that contains 4 to about 15 carbon atoms and one, two or three saturated or unsaturated rings in which up to three atoms per ring that are other than carbon and can be oxygen, nitrogen or sulfur. Aromatic ring compounds are preferred and include phenyl, a naphthyl, a phenanthryl, an anthracenyl, 7-isoquinolinyl, quinolinyl, pyridinyl (pyridyl), pyrimidinyl, pyrazinyl, triazinyl, furanyl (furyl), thiophenyl, benzofuranyl, isobenzofuranyl, benzothiofuranyl, a pyridopyridinyl or the like. The previously noted moieties can be bonded to the depicted carbon atom (C-17 in steroidal numbering) through multiple ring atoms, and each of those isomers is contemplated herein. Such moieties provide the corresponding cyclic or heterocylic derivative of the Formula XII, wherein $R^1$ and $R^5$ are as before, and the circled X is a cyclic or heterocyclic substituent that contains 4 to about 15 carbon atoms, contains one to three saturated or unsaturated rings and up to three atoms per ring that are other than carbon and can be oxygen, nitrogen or sulfur. Circled X is preferably an aromatic moiety.

XII

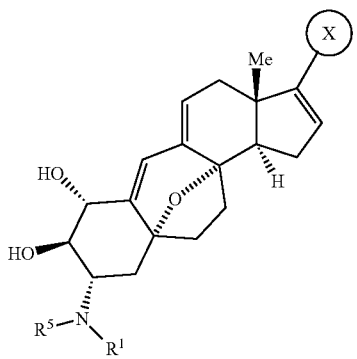

Raney nickel reduction of the resulting compound of Formula XII provides the desired stereoisomeric cortistatin compound of Formula XIII, wherein $R^1$, $R^5$ and the circled X are as before. Where $R^1$ and $R^5$ are both methyl and the circled X is a 7-isoquinolinyl, the compound of Formula XIII is (+)cortistatin A (1). Thus, a compound of Formula XIII other than where (i) $R^1$ and $R^5$ are both methyl and (ii) the circled X is a 7-isoquinolinyl group is a compound contemplated herein.

XIIIb

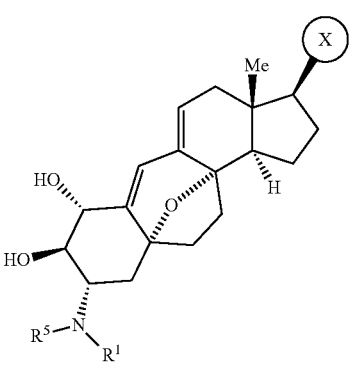

XIIIa

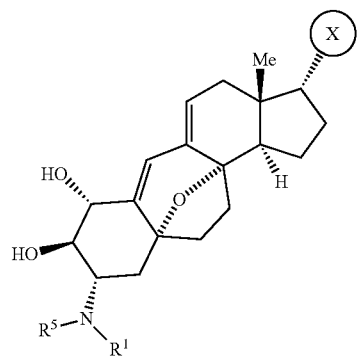

XIII

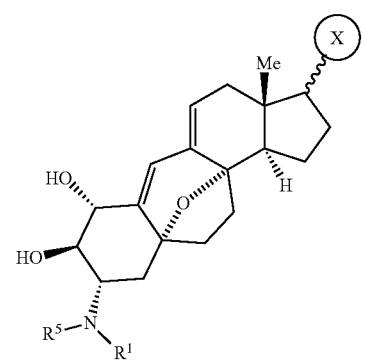

It is noted that a β-configured circled X compound of Formula XIIIb and its epimeric α-configured isomer of Formula XIIIa can be formed by one or more alternative routes to that shown above. A compound with an unspecified configuration for the circled X substituent; i.e., a compound whose circled X moiety is in the α-configuration, the β-configuration or a mixture of both configurations, is depicted by Formula XIII in which the circled X substituent is joined to the rest of the molecule by a wavy line. One particularly successful route using an aromatic circled X substituent is shown in the Scheme A below in which the stereoconfiguration of the circled X aromatic group bonded at C-17 can be prepared in either of the α- and β-configurations.

Scheme A

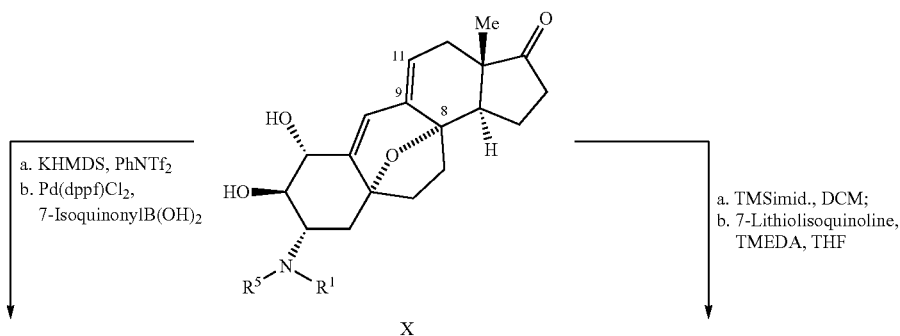

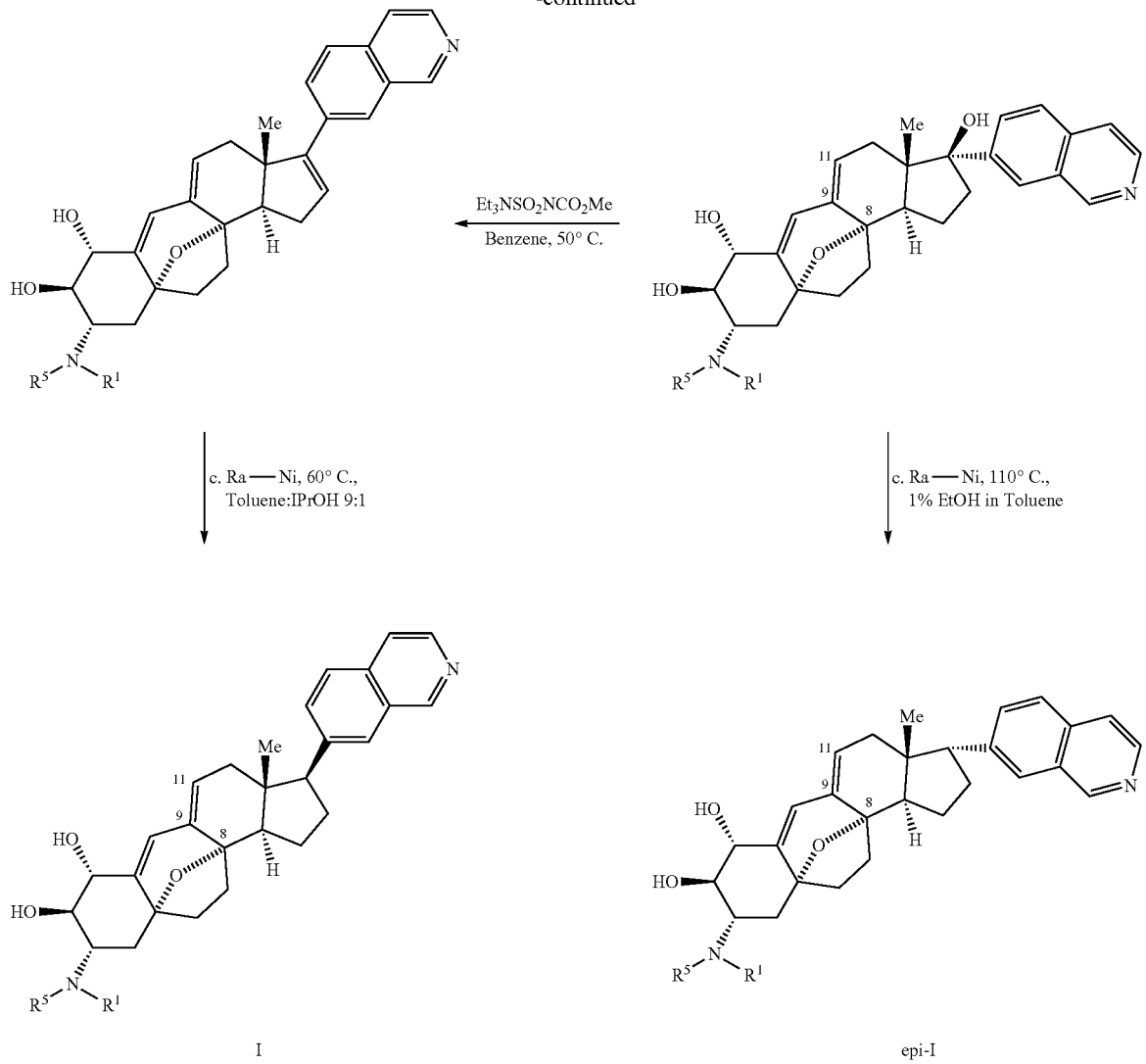

Thus, in the synthesis outlined previously, a Stille coupling was utilized to add the circled X moiety to the steroidal compound. As shown above, a lithio salt can be used to add to the keto group as can a Suzuki coupling using a boronic acid derivative. As is also seen, Raney nickel can be used to hydrogenate the double bond as well as to deoxygenate the hydroxyl compound. The above Scheme A also illustrates two syntheses of the unsaturated ($\Delta^{16}$) 17-substituted cortistatin type compound. As is discussed below, $\Delta^{16}$-cortistatin A has a biological activity that is substantially the same as that of (+)cortistatin A.

Model studies using 3-(tert-butyldimethylsilyl)hydroxy-estrone as the steroidal framework instead of a cortistatinone framework have illustrated the generality of the synthetic methods shown above with a variety of aromatic 17-substituent moieties. The isolated yields for the formation of the 17-aryl α- or β-substituents in the model reaction system and the diastereoselectivity for those reactions are shown in the Table below along with the 17-aryl substituent utilized.

| 17-Substituent | α-Isolated Yield (%) | Diastereo-selectivity | β-Isolated Yield (%) | Diastereo-selectivity |
| --- | --- | --- | --- | --- |
| Phenyl | 98 | 6.6:1 | 97 | >20:1 |
| 4-Methylphenyl | 88 | >20:1 | 98 | >20:1 |
| 4-Methoxyphenyl | 68% | 4.2:1 | 93 | >20:1 |
| 7-Isoquinolinyl | 71 | 4.3:1 | 68 | >20:1 |
| 3-Pyridyl | 72 | 13:1 | 72 | >20:1 |
| 4-Fluorophenyl | — | — | 93 | >20:1 |
| 4-Trifluoromethylphenyl | — | — | 96 | >20:1 |

Biological Activity

In an assay to determine activity against HUVECs (carried out by Pfizer, Inc.), synthetic cortistatin A exhibited an $IC_{50}$ value of 2.43 nM, which is in good agreement with the reported value. [Aoki et al., *J. Am. Chem. Soc.* 2006, 128: 3148-3149] Remarkably, $\Delta^{16}$-cortistatin A retains high potency against HUVECs, with an $IC_{50}$ of 3.88 nM being very similar to that of the parent compound itself. This result is a significant step forward in the simplification of the overall cortistatin structure from a synthesis standpoint. Interestingly, 17-epi-cortistatin A (epi-I) in which the 7-isoquinolinyl group is in the α-configuration does not exhibit useful levels of activity (>1 mM). These results are shown in the Table below.

TABLE

| Substrate | $IC_{50}$ (nM) |
|---|---|
| cortistatin A | 2.43[a], 1.8[b] |
| $\Delta^{16}$-cortistatin A | 3.88 |
| 17-epi-cortistatin A | >1000 |

[a] $IC_{50}$ of synthetic cortistatin A tested by Pfizer, Inc.
[b] $IC_{50}$ of natural cortistatin A tested by Kobayashi group.[4a]

Illustrative Synthesis

In a specific, illustrative synthesis, prednisone, was converted to the known steroid core Compound 9 (Scheme 1, below)

Scheme 1

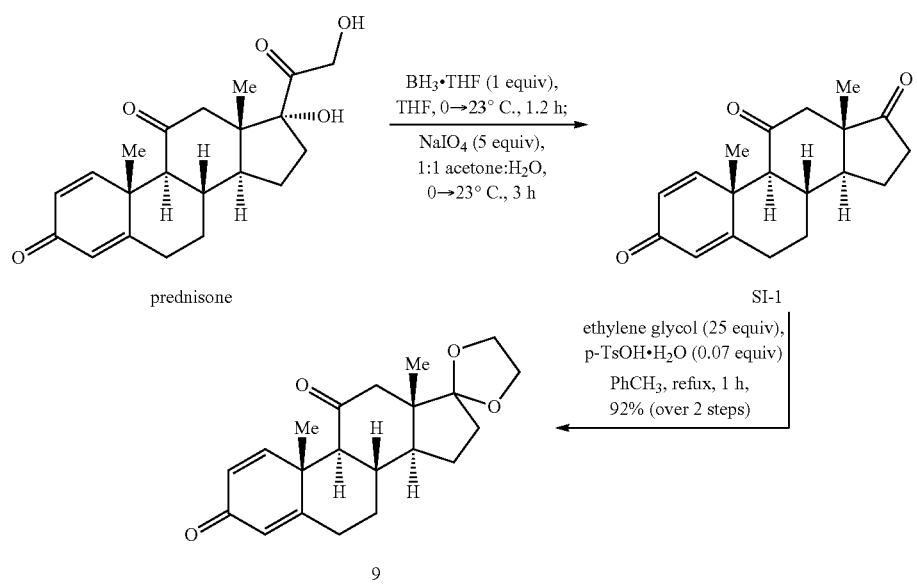

in a short two-step sequence, and in 92% overall yield after recrystallization. The C1,C2 trans-vicinal diol was targeted through the intermediacy of α-disposed epoxyformamide Compound 10, which was installed using tert-butyl hydroperoxide instead of the precedented, but non-scalable dimethyldioxirane (DMDO) procedure [Bovicelli et al., *J. Org. Chem.* 57:2182 (1992)]. Reductive amination of the unsaturated ketone proceeded uneventfully, and refluxing the crude reaction mixture with ethyl formate generated epoxyformamide Compound 10 in good yield (steps a. and b. of Scheme 2, below).

Scheme 2

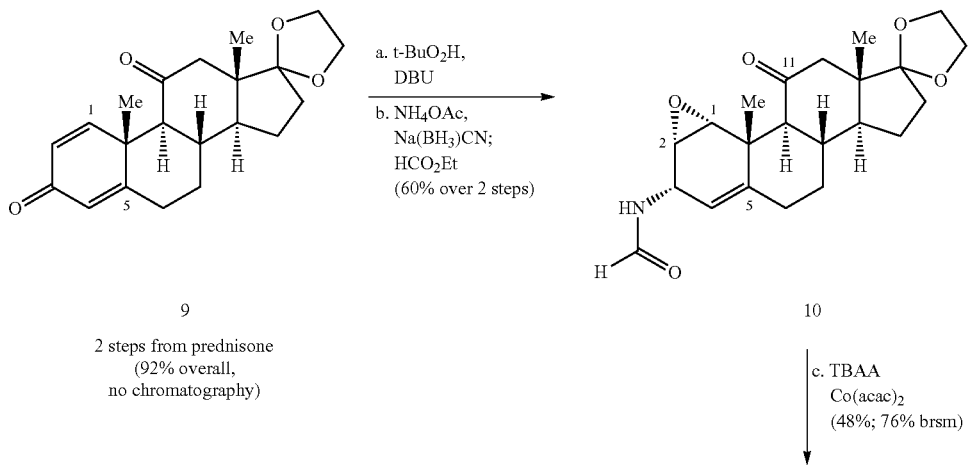

-continued

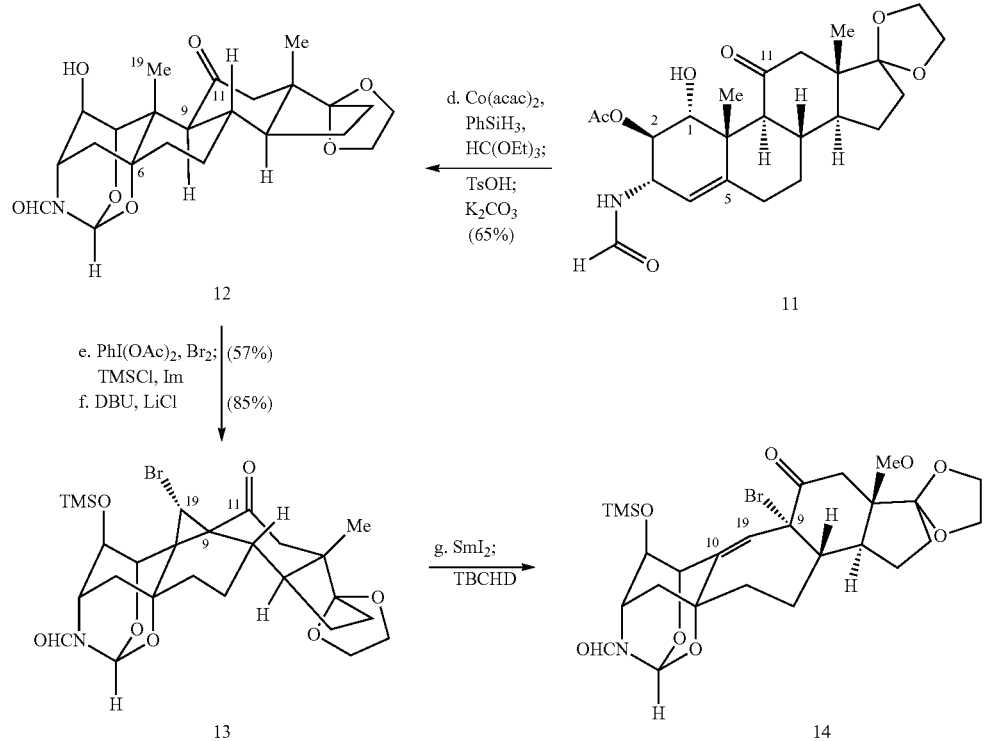

The epoxide, however, proved intractable to a number of standard procedures for nucleophilic addition. Under acidic aqueous conditions the nascent diol underwent facile cyclization onto the C11 ketone, followed by dehydration to yield an unproductive dihydrofuran, which itself is a rare motif among steroids [Halsall et al., *J. Chem. Soc., Perkin Trans.* 1 1758 (1975)]. Conversely, basic aqueous conditions led to undesired cleavage of the formyl moiety, a group that would figure prominently as a methyl-surrogate of the target molecule. Eventually, it was found that tetra-n-butylammonium acetate (TBAA) in refluxing benzene opened the epoxide at C2, producing the trans-hydroxy acetate Compound 11 (step c. of Scheme 2).

After extensive experimentation, it was found that the key orthoamide Compound 12 could be synthesized in one pot from intermediate Compound 11 by use of the following reactions 1) Mukaiyama hydration of the trisubstituted olefin; 2) reaction of the amidodiol with trimethyl orthoformate; and 3) solvolysis of the C2-acetate (step d. of Scheme 2). Notably, reacting epoxyformamide Compound 10 under identical conditions for Mukaiyama hydration gave a 5:1 stereoisomeric mixture of tertiary alcohols, disfavoring the desired C5 α-stereochemistry. The heteroadamantane core thus generated not only shields the majority of A-ring functionality, it also rigidifies the carbon skeleton for the ensuing unconventional chemical reactions.

During preliminary reconnaissance in accessing the cortistatin core, the most difficult functionality to secure turned out to be the C19 methine oxidation state, suggesting the importance of its installation early in the sequence. [For the first examples of angular methyl oxidation of a steroid, see Corey et al., *J. Am. Chem. Soc.* 80:2903 (1958); Buchschacher et al., *J. Am. Chem. Soc.* 80:2905 (1958).] Unfortunately, existing methods for such a transformation (angular methyl→aldehyde oxidation state) are reported to give generally low yields [Godula et al., *Science* 312:67 (2006)], and more importantly, proved completely ineffectual in our system.

Consequently, a new process was conceived to access a dibrominated 19-carbon, utilizing in situ-generated acetoxy hypobromite (AcOBr) [González et al., *Tetrahedron Lett.* 44, 6347 (2003)]. Success was realized by significantly lowering the reaction temperature, and extending the reaction time, resulting in an iterative, double methyl activation (Scheme 3 that shows the A rings only of Compounds Scheme 3

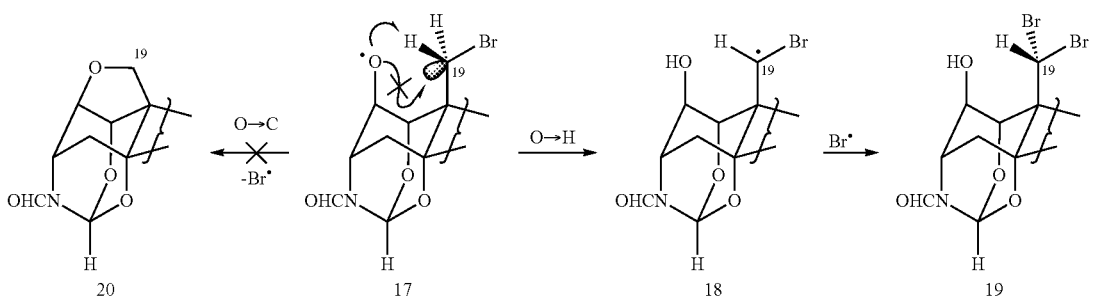

17→18→19), while suppressing $S_N2$ attack of the alcohol on the $\sigma^*_{C-Br}$ orbital of the monobromide [Cekovic, *Tetrahedron* 59:8073 (2003)] (17→20; possibly $S_H2$ attack of the transient O-centered radical).

This reaction is believed to be the first example of an alcohol-directed, geminal dihalogenation of an unactivated hydrocarbon. The selectivity for dibromination (57%) over mono- or tribromination well surpasses what would be expected with only the governance of statistics [McQuarrie et al., *Physical Chemistry: A Molecular Approach*. (University Science Books, Sausolito, Calif., 1997)], which would produce the dihalide in a maximum yield of 27%. Use of the well-precedented $PhI(OAc)_2/I_2$ conditions for monoiodination [Cekovic, *Tetrahedron* 59:8073 (2003)] resulted in competitive THF formation, likely due to a much larger coefficient of the $\sigma^*_{C-I}$ orbital.

The unstable dibromo alcohol (Compound 19, Scheme 3) was capped with a trimethylsilyl group to prevent intramolecular cyclization. Alkylation of the 9,11-enolate with the proximal dibromomethyl proceeded with DBU and lithium chloride to provide one bromocyclopropane diastereomer Compound 13 (step d. of Scheme 2) whose configuration was confirmed by x-ray diffraction of alcohol derivative Compound 13'.

After extensive experimentation, a cascade sequence (step e. of Scheme 2) was developed to achieve isomerization of bromocyclopropane Compound 13 to cycloheptyl α-bromoketone Compound 14 in high yield. This transformation was accomplished as illustrated in Scheme 4, below, by radical opening of the 3-membered ring (Compounds 21→22), extrusion of bromine radical (Compound 22→23), and trapping of dienolate Compound 23 with 2,4,4,6-tetrabromo-2,5-cyclohexadienone (TBCHD) [Sakamaki et al., *J. Org. Chem.* 53:2622 (1988); Neef et al., *Tetrahedron* 49:833 (1993)].

Scheme 4

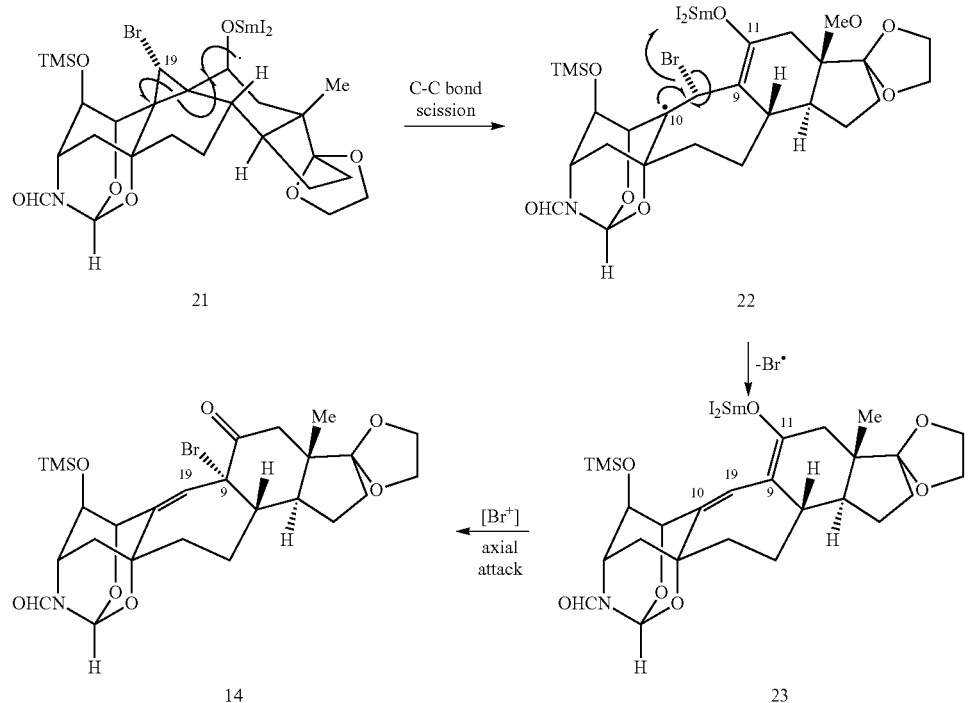

The major diastereomer of the reaction is likely the α-disposed allylic, C-9-bromide Compound 14: although spectroscopy could not assign this stereochemistry unambiguously, ensuing reactions and stereoelectronic considerations [Corey, *J. Am. Chem. Soc.* 76:175 (1954); Corey et al., *J. Am. Chem. Soc.* 78:6269 (1956)] suggest this configuration. Thus, the oxidation state deliberately embedded in the 19-methyl dibromide Compound 19 translated smoothly into the olefinic C19-methine of the cortistatin core. Without the carefully placed bromine atom in the cyclopropane ring of Compound 13, this fragmentation led to intermediates that could not be converted to the desired dienone Compound 16, as is illustrated in the Examples.

Elimination of the α-bromide Compound 14 with lithium carbonate delivered the cross-conjugated dienone Compound 16. Under the action of alane, the heteroadamantane A-ring core was reductively unmasked to reveal the entire A-ring of cortistatin A; in situ desilylation and triacetylation delivered dimethylamino triacetate Compound 15 as a diastereomeric mixture at C11. The reactions leading from Compound 14 to Compound 15 are shown in Scheme 2B, below, (steps h. and i. of Scheme 5). A repeated synthesis of Compounds 13 to 15 provided a yield of 58% over three steps.

Scheme 5
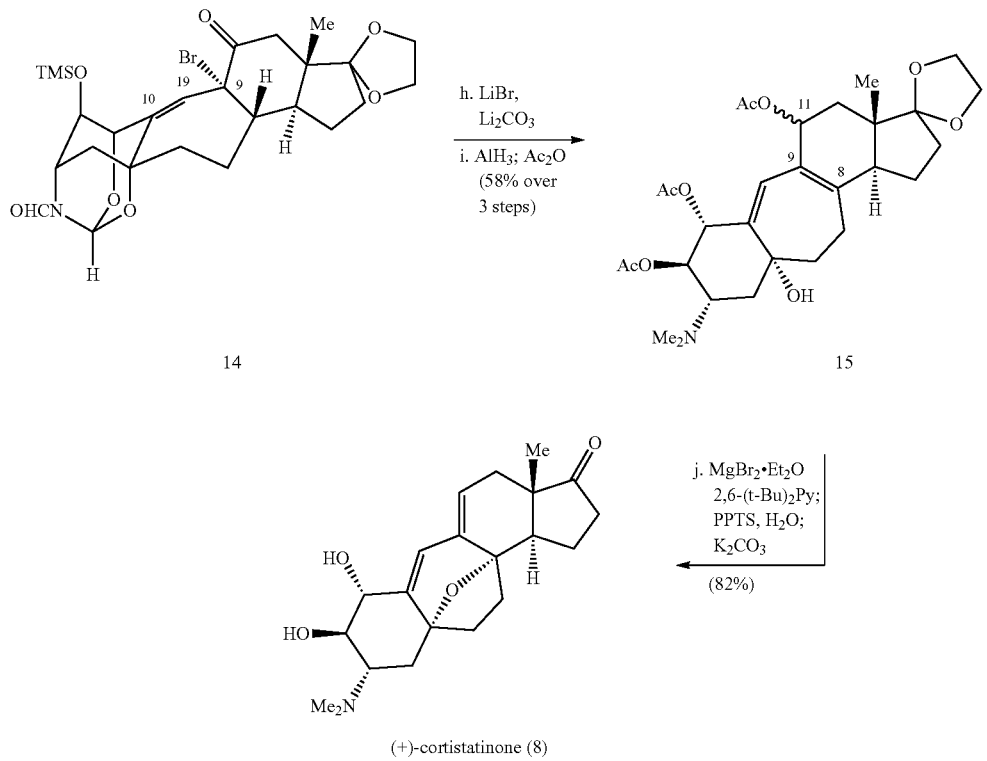
A different view of portions of the above synthesis is illustrated in Scheme 5A, below, provided Compound 16 in a 65% yield over two steps.
Scheme 5A
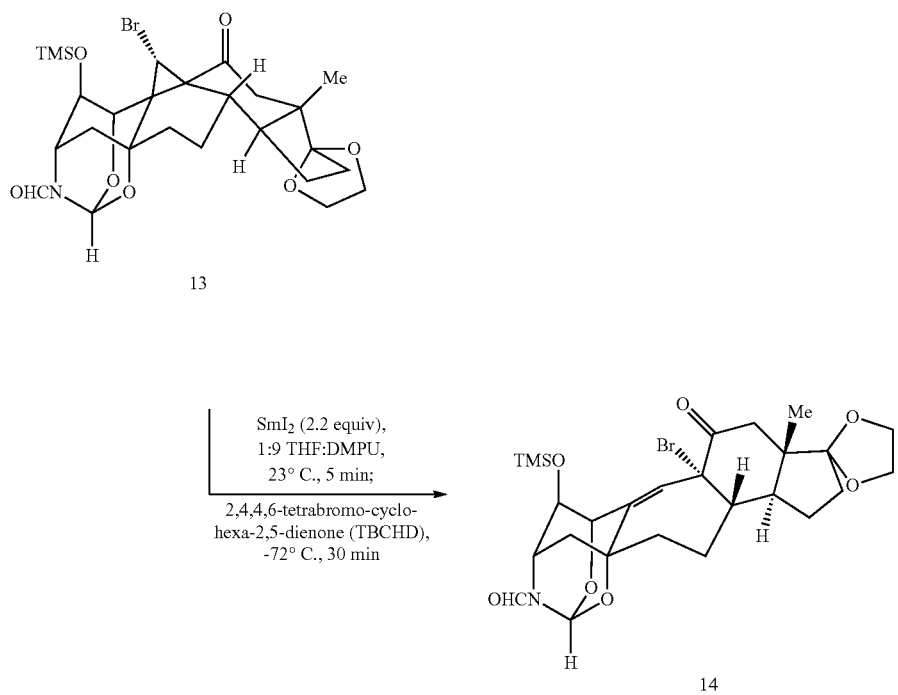

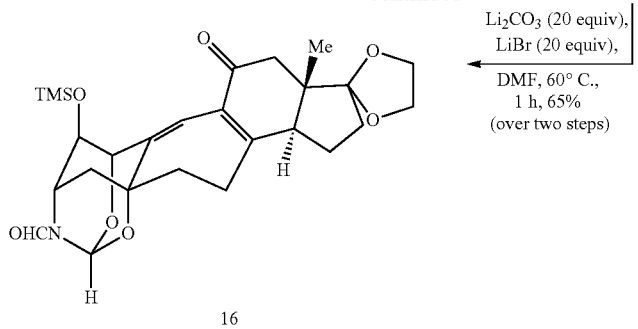
Acetylation of the C11-alcohol served to activate the 8,9-olefin towards conjugate displacement, which was achieved upon heating with MgBr$_2$.Et$_2$O in benzene, delivering the bridging bicyclic ether of the cortistatin core (Compound SI-4, Scheme 6) in high yield. The reaction likely
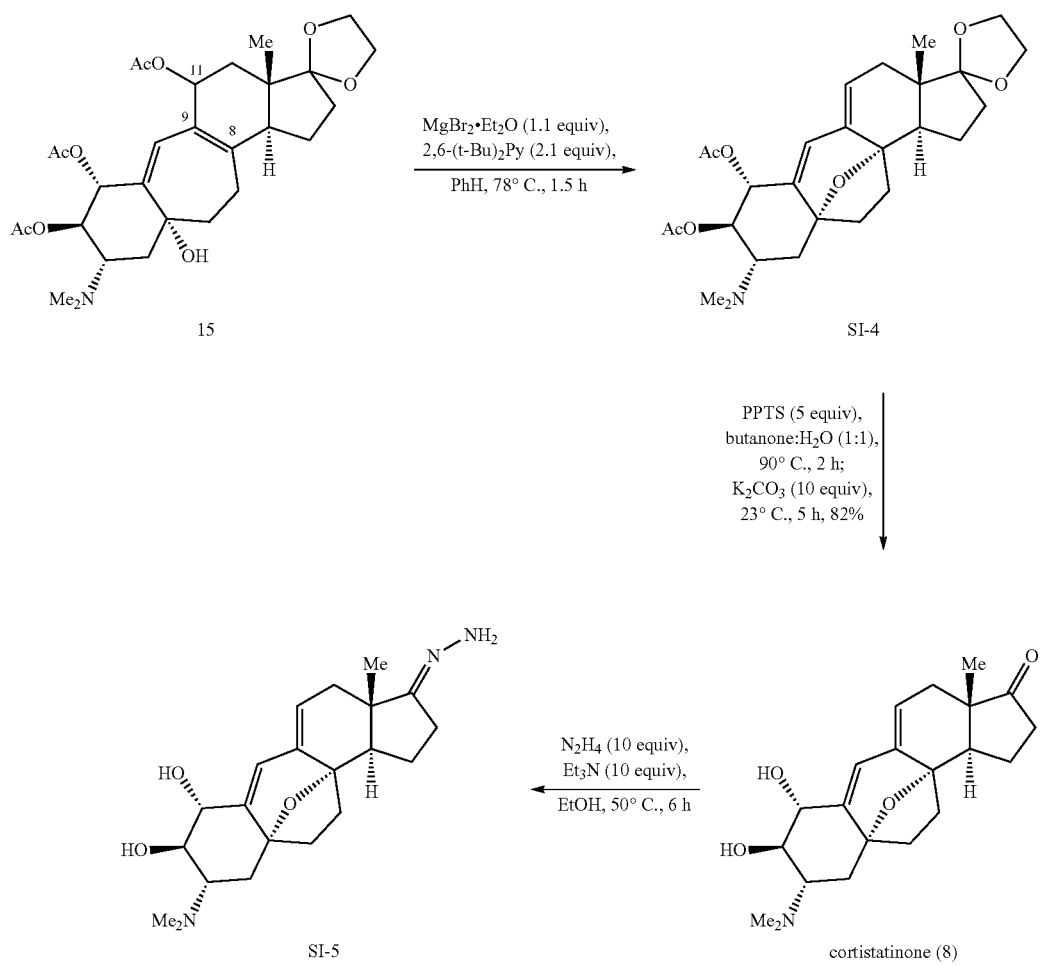

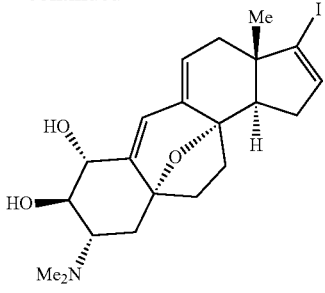

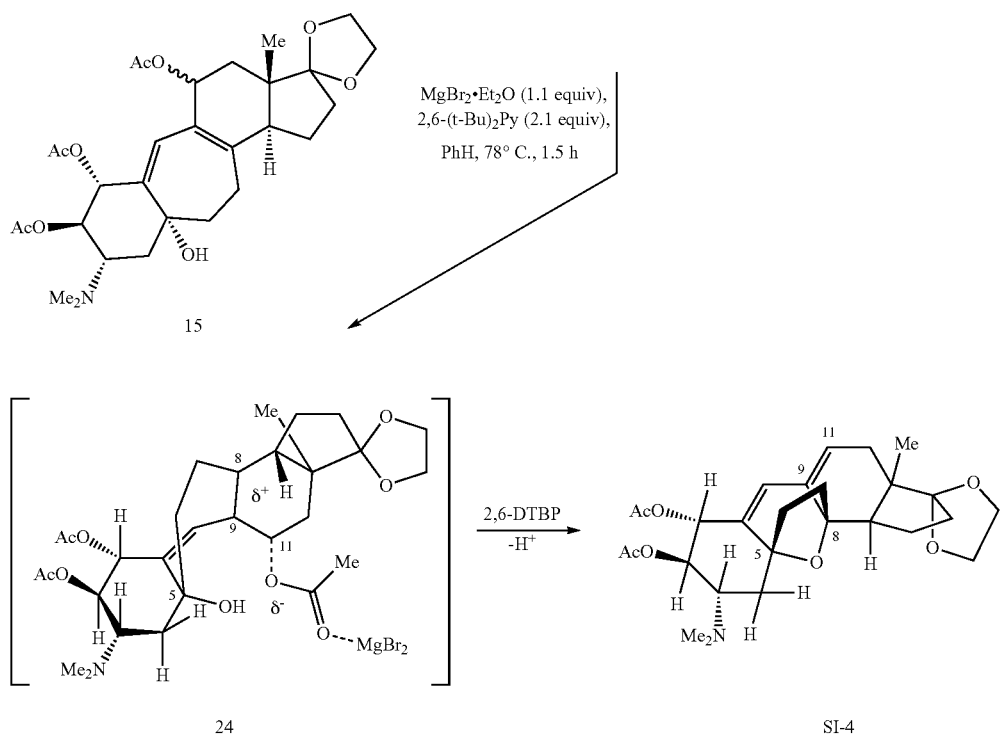

proceeds via initial Lewis acid-catalyzed partial ionization of the C11-acetate, followed by allylic displacement at C8 by the C5-tertiary alcohol presumably as shown in Scheme 6A (below; Compounds 15→24→SI-4).

The acetate at C1 may be resistant to ionization due to its equatorial disposition, lying nearly perpendicular to the diene π-system. Mild deketalization using pyridinium p-toluenesulfonate, followed by solvolytic removal of the A-ring acetates delivered (+)-cortistatinone (Compound 8), whose proton and carbon NMR spectra bore a satisfying similarity to the reported spectra for cortistatin A.

To complete the synthesis, a challenging task lay ahead: appending the requisite β-disposed C17-isoquinoline in the presence of a tertiary amine, a vicinal diol, two olefins, and a sensitive bridging oxacycle. Those objectives were achieved using the following sequence that is shown in Scheme 7, below.

Scheme 7

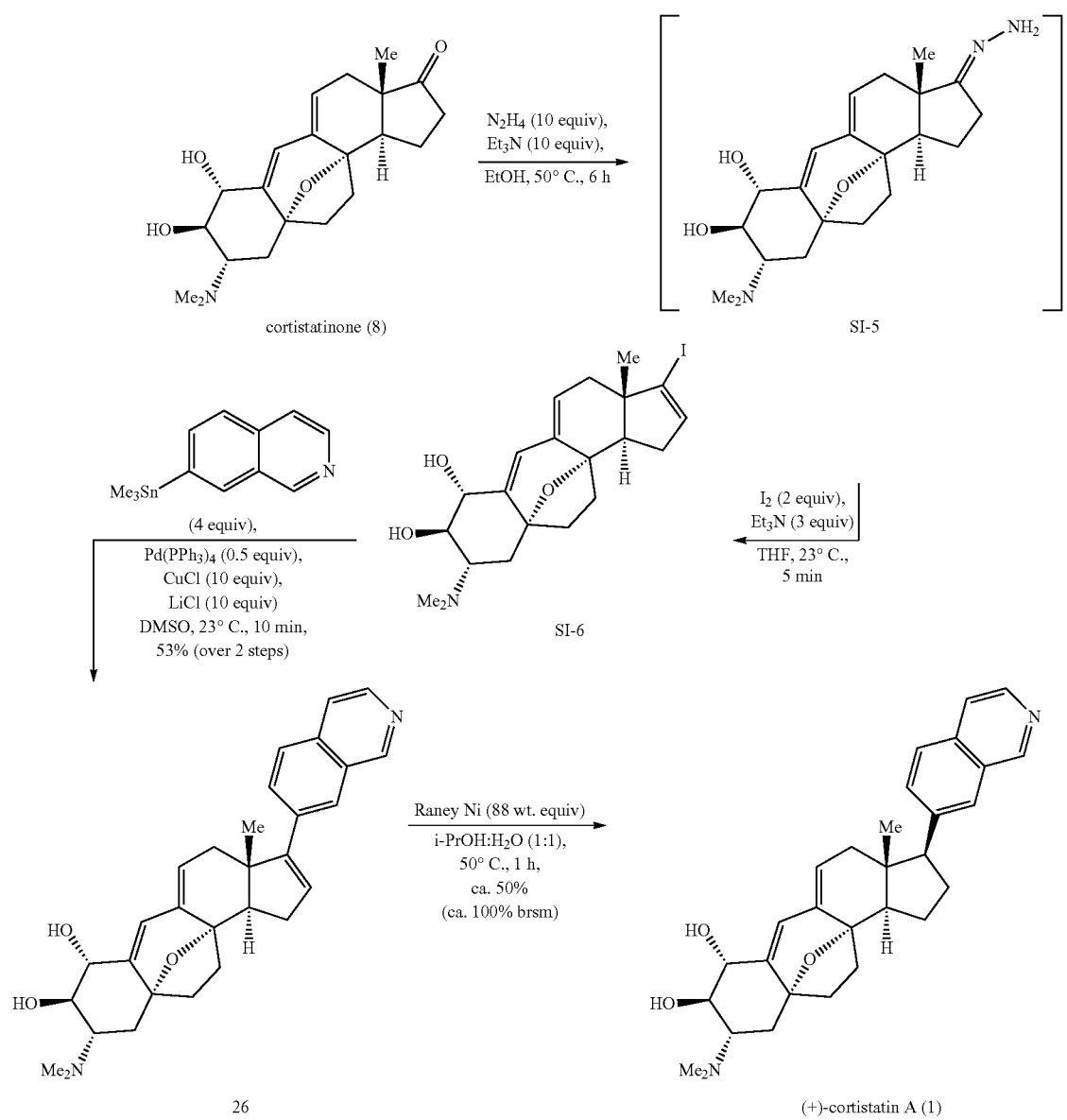

First, cortistatinone (Compound 8) was treated with hydrazine to form an intermediate $C_{1-7}$ hydrazone, which was not isolated, but rather immediately subjected to iodine and triethylamine to form an alkenyl iodide [Barton et al., J. Chem. Soc. 470 (1962)], sparing both the C3 tertiary amine and the internal diene. Second, Stille coupling delivered the conjugated isoquinoline Compound 26 without incident; it is projected that this reaction should be amenable to the installation of numerous heterocyclic side chains. Finally, in a consummate example of chemoselective reduction, the benzylic olefin was reduced with Raney Nickel in water and isopropanol to yield synthetic (+)cortistatin Compound 1, whose spectral characteristics were identical to those reported in the literature.

Interestingly, studies on an estrone model system (shown in the Examples hereinafter) displayed a striking stereochemical dichotomy between hydrogenating benzylic olefin Compound 27 and deoxygenating benzylic alcohol Compound 28, yielding 17-β- and 17-α-isoquinolines Compounds 29 and 30, respectively. The exploration and mechanistic study of this phenomenon is underway. Preliminary studies on the corresponding tertiary benzylic alcohol in cortistatin (17-hydroxy-17-epi-cortistatin A) have confirmed this deoxygenation strategy as a viable route to 17-epi-cortistatin A, whose biological activity we plan to report in the future.

Thus, (+)-cortistatin A (Compound 1), the most biologically active member of the marine-derived cortistatin family was synthesized in 15 linear steps (ca. 3%, overall yield, unoptimized) from the inexpensive terrestrial steroid prednisone, which is commercially available in multi-kilogram quantities. With several reactions left unoptimized, we have already prepared over 100 mg of (+)-cortistatinone (Compound 8) that is poised for the synthesis of a multitude of D-ring analogs. As it stands, all carbon atoms in Compound 1 are amenable to simple modification (analog synthesis) with the exception of C-6, 7, and 14.

Certain aspects of this synthesis carry important lessons in chemical reactivity, selectivity, and synthesis strategy, including: 1) the four step sequence (Compounds 9-*12) to install all requisite A-ring stereochemistry; 2) a newly invented alcohol-directed, dibromination reaction (Compounds 12→19); 3) an isohypsic radical cascade (Compounds 13→14) to access the 9-(10,19)-abeo-androstane skeleton; 4) an olefin-sparing, heteroadamantane fragmentation to differentiate the tethered aminodiol; 5) a mild $S_N$-prime cyclization to close the final ring of the cortistatin skeleton (Compounds 15→28); 6) a selective benzylic hydrogenation to facilitate the transformation of (+)-cortistatinone to (+)-cortistatin A (Compounds 8→1); and 7) a minimal reliance on protecting groups in the context of complex molecular transformations.

Access to Compound 8 will prove valuable in probing the crucial [Aoki et al., *Bioorganic & Medicinal Chemistry* 15, 6758 (2007)] heterocyclic domain of the cortistatins; targeting this intermediate should also facilitate future syntheses. Collaborations are now underway to establish the anti-angiogenic mode of action of cortistatin A and analogs thereof.

EXAMPLES

General Procedures

All reactions were carried out under an inert nitrogen atmosphere with dry solvents under anhydrous conditions unless otherwise stated. Dry tetrahydrofuran (THF), dichloromethane ($CH_2Cl_2$), benzene (PhH), toluene ($PhCH_3$), methanol (MeOH), acetonitrile, N,N-dimethylformamide (DMF), and triethylamine ($Et_3N$) were obtained by passing these previously degassed solvents through activated alumina columns. Reagents were purchased at the highest commercial quality and used without further purification, unless otherwise stated. Raney nickel was purchased from Sigma Aldrich (as Raney 2800 nickel) and was stored at 4° C. It was either used directly or washed before use, as detailed in the experimental procedures (vide infra). Yields refer to chromatographically and spectroscopically ($^1$H NMR) homogeneous materials, unless otherwise stated. Reactions were monitored by thin layer chromatography (TLC) carried out on 0.25 mm E. Merck silica gel plates (60F-254) using UV light as the visualizing agent and an acidic mixture of anisaldehyde, phosphomolybdic acid, or ceric ammonium molybdate, or basic aqueous potassium permanganate ($KMnO_4$), and heat as developing agents. E. Merck silica gel (60, particle size 0.043-0.063 mm) was used for flash column chromatography. Preparative thin layer chromatography (PTLC) separations were carried out on 0.25 or 0.5 mm E. Merck silica gel plates (60F-254). NMR spectra were recorded on Bruker DRX-600, DRX-500, and AV-400 instruments and calibrated using residual undeuterated solvent as an internal reference ($CHCl_3$ @ 7.26 ppm $^1$H NMR, 77.0 ppm $^{13}$C NMR). The following abbreviations (or combinations thereof) were used to explain the multiplicities: s=singlet, d=doublet, t=triplet, q=quartet, m=multiplet, b=broad, a=apparent. High-resolution mass spectra (HRMS) were recorded on Agilent LC/MSD TOF (time-of-flight) mass spectrometer by electrospray ionization time of flight reflectron experiments. IR spectra were recorded on a Perkin Elmer Spectrum BX FTIR spectrometer. Melting points were recorded on a Fisher-Johns 12-144 melting point apparatus.

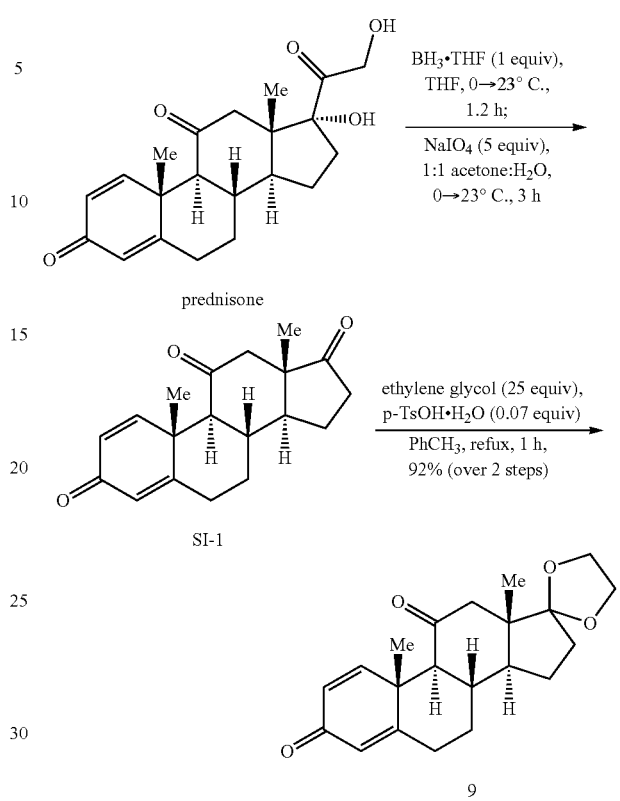

Dienone Compound 9:

To a suspension of prednisone (53.3 g, 149 mmol) in anhydrous THF (496 mL, 0.3 M) was added $BH_3$·THF (1 M in THF, 149 mL, 149 mmol, 1.0 equiv) via syringe over 30 minutes at zero ° C. After the reagent addition was complete, the cooling bath was removed. The suspension gradually turned into a clear solution. After 20 minutes, additional $BH_3$·THF (1 M in THF, 7.4 mL, 7.4 mmol, 0.05 equiv) was added. After another 20 minutes, all starting material had been consumed. The reaction was cooled to zero ° C. and approximately 500 mL of 1:1 acetone:water was added slowly.

Then $NaIO_4$ (159 g, 743 mmol, 5 equiv) was added over 5 minutes. The resulting suspension was stirred vigorously for 3 hours at ambient temperature, during which time the reaction thickened and became difficult to stir. After the reaction was complete, the suspension was filtered over Celite and evaporated until the majority of acetone and THF had been removed. The resulting suspension was extracted with EtOAc (500 mL). The aqueous portion was extracted three more times with EtOAc (3×200 mL). The combined organic portions were washed with sat. aq. $Na_2S_2O_3$ (500 mL), water (500 mL) and sat. aq. NaCl (500 mL). The solution was dried over $MgSO_4$ and concentrated to give an off-white solid that was sufficiently pure for ketalization.

Note: the triol cleavage can be accomplished with as few as 2 equivalents of $NaIO_4$, but this requires stirring overnight (about 18 hours) for full consumption of the triol.

One fourth of the trione so produced was ketalized as follows: to this portion of crude trione as a suspension in toluene (620 mL, 0.06 M) was added ethylene glycol (52 mL, 929 mmol, 25 equiv) and p-TsOH·$H_2O$ (513 mg, 2.69 mmol, 0.0725 equiv). The reaction vessel was incorporated into a standard Dean-Stark setup and immersed in an oil bath preheated to 135° C. and stirred vigorously. After 55 minutes, the reaction vessel was lifted out of the oil bath and permitted to cool. The layers were permitted to settle and the ethylene glycol was separated from the organic layer; this layer was neutralized with sat. aq. NaHCO$_3$ (100 mL) and the layers were again separated. The aqueous portion was extracted twice with EtOAc (2×100 mL). The organic portions were combined, washed with sat. aq. NaCl (200 mL), dried over MgSO$_4$, and concentrated. The remaining trione was ketalized in the same manner and the crude portions were combined and crystallized by boiling in EtOAc to effect dissolution, followed by cooling at 4° C. The first recrystallization furnished 37.25 g, the second 7.63 g, and the third 1.81 g, for a total of 46.69 g (92%) of the known title compound.

Note: the heating time for the ketalization is specific for the scale specified. The reaction was conducted in a 1 L round bottom flask immersed in a 190 mm (diameter)×100 mm (depth) oil bath. The heating time reflects a balance between full consumption of starting material and over-ketalization.

Epoxy enone Compound SI-2:

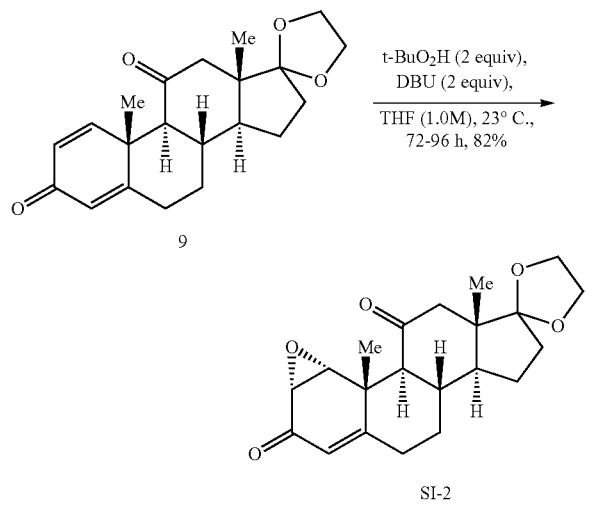

To a solution of dienone Compound 9 (100 g, 292 mmol) in THF (292 mL, 1.0 M) was added 70% aq. TBHP (80 mL, 484 mmol, 2.0 equiv) and DBU (80 mL, 535 mmol, 1.83 equiv) and the reaction mixture was stirred at ambient temperature for 72 hours. The reaction mixture was quenched by the addition of aq. Na$_2$S$_2$O$_3$ (300 mL) and stirred vigorously for 2 hours. The resulting biphasic mixture was extracted twice with EtOAc (2×600 mL). The organic portions were combined, washed twice with sat. aq. Na$_2$S$_2$O$_3$ (2×200 mL) and once with water (200 mL) and sat. aq. NaCl (200 mL), dried over MgSO$_4$ and concentrated in vacuo. The residue so obtained was purified by flash column chromatography (silica gel, hexanes:EtOAc 2:1) furnishing epoxy enone Compound SI-2 (85.8 g, 82%) as a white solid: R$_f$=0.41 (1:1 hexanes:EtOAc); [α]$_D$=+184.8° (c 1.69, CH$_2$Cl$_2$); IR (neat) ν$_{max}$=2942, 2880, 1702, 1672, 1624, 1176, 1103, 1042, 879, 752 cm$^{-1}$; $^1$H NMR (500 MHz, CDCl$_3$) δ 5.65 (t, J=1.8 Hz, 1H), 4.25 (d, J=3.9 Hz, 1H), 3.92-3.86 (m, 2H), 3.81-3.75 (m, 2H), 3.33 (dd, J=4.0, 2.0 Hz, 1H), 2.68 (d, J=12.5 Hz, 1H), 2.43 (tdd, J=14.0, 4.9, 2.0 Hz, 1H), 2.37 (d, J=11.5 Hz, 1H), 2.28-2.24 (m, 1H), 2.11 (d, J=12.5 Hz, 9H), 2.07-1.98 (m, 2H), 1.95-1.85 (m, 3H), 1.82-1.79 (m, 1H), 1.42 (s, 3H), 1.39-1.29 (m, 1H), 1.24-1.15 (m, 1H), 0.83 (s, 3H); $^{13}$C NMR (125 MHz, CDCl$_3$) δ 209.6, 193.7, 164.1, 120.5, 117.3, 65.3, 64.5, 60.5, 58.2, 55.0, 49.5, 49.1, 48.4, 40.1, 36.7, 34.0, 32.3, 31.5, 22.1, 18.6, 14.9; HRMS (ESI-TOF) calcd for C$_{21}$H$_{26}$O$_5$ [M+H]$^+$: 359.1853; found: 359.1868.

Epoxy formamide Compound 10:

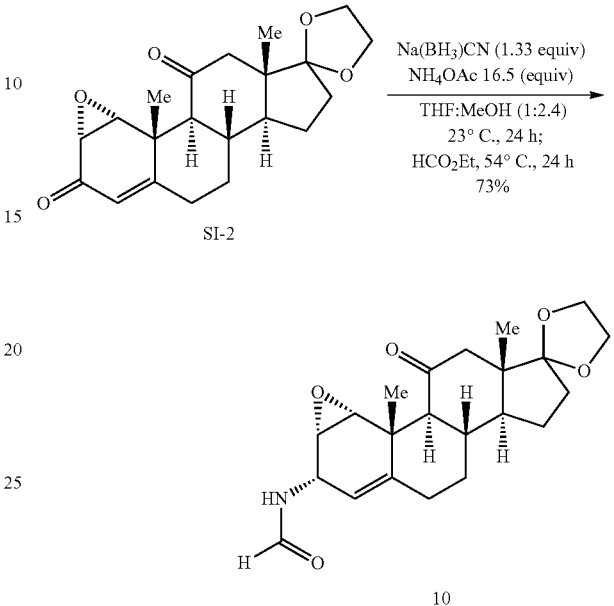

To a solution of NH$_4$OAc (170 g, 2.21 mol, 16.5 equiv) in MeOH (1.3 L, 0.103 M) was added NaBH$_3$CN (11.2 g, 178 mmol, 1.33 equiv) and the reaction mixture was stirred at ambient temperature for 10 minutes (the mixing is endothermic; the reaction mixture can be warmed gently with a heat gun). Then a solution of epoxy enone Compound SI-2 (48.0 g, 134 mmol) in THF (536 mL, 0.25 M) was added by cannula. The reaction was stirred at ambient temperature for 18 hours. Ethyl formate (800 mL) was then added, followed by Et$_3$N (200 mL). The reaction mixture was heated at reflux for approximately 12 hours, permitted to cool to ambient temperature and concentrated in vacuo. The residue so obtained was purified by flash column chromatography (silica gel, CH$_2$Cl$_2$:acetone 5:1) furnishing 38.0 g (73%) of epoxy formamide Compound 10 as off white free flowing micro-crystals: R$_f$=0.40 (100% EtOAc); [α]$_D$=+75.4° (c 2.33, CH$_2$Cl$_2$); IR (neat) ν$_{max}$=3310, 2936, 1701, 1521, 1173, 1104, 1042, 919, 735 cm$^{-1}$; (All compounds containing this formamide exhibit two rotamers about the C$_{(carbonyl)}$—N bond in their NMR spectra at ambient temperature; only the major rotomer is described.) $^1$H NMR (600 MHz, CDCl$_3$) δ 8.21 (s, 1H), 5.85 (d, J=8.4 Hz, 1H), 4.95-4.93 (m, 2H), 3.97 (d, J=3.6 Hz, 1H), 3.94-3.88 (m, 2H), 3.83-3.78 (m, 2H), 3.41-3.40 (m, 1H), 2.68 (d, J=12.0 Hz, 1H), 2.25-2.21 (m, 1H), 2.17 (d, J=11.5 Hz, 1H), 2.10-2.01 (m, 4H), 1.93-1.88 (m, 1H), 1.84-1.78 (m, 3H), 1.40-1.33 (m, 1H), 1.32 (s, 3H), 1.10-1.04 (m, 1H), 0.83 (s, 3H); $^{13}$C NMR (150 MHz, CDCl$_3$) δ 210.6, 160.4, 141.9, 117.6, 115.7, 65.4, 64.6, 59.2, 57.5, 54.9, 49.7, 49.2, 48.8, 42.8, 37.0, 37.0, 34.2, 31.8, 31.5, 22.2, 17.8, 14.9; HRMS (ESI-TOF) calcd for C$_{22}$H$_{29}$NO$_5$ [M+H]$^+$: 388.2118; found: 388.2126.

Acetoxy hydroxy formamide Compound 11:

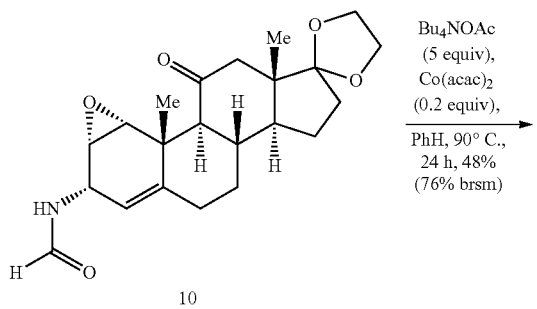

Orthoamide alcohol Compound 12:

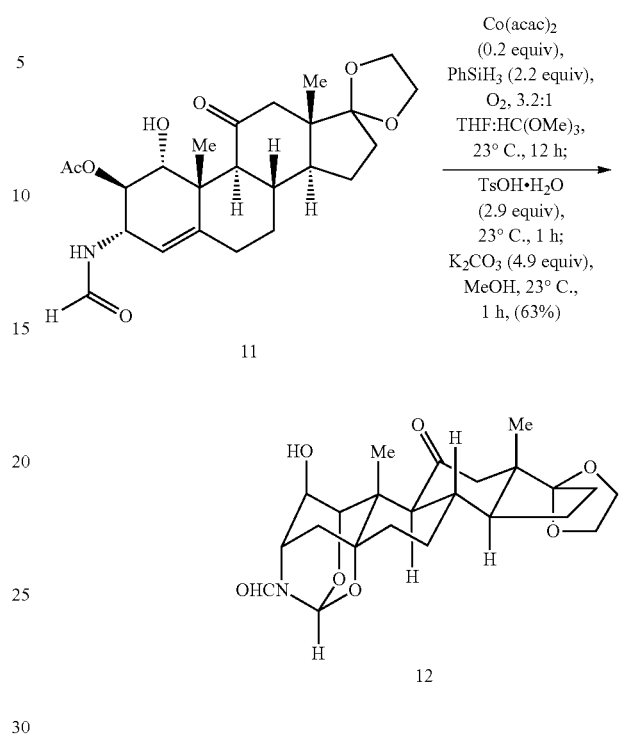

To a solution of epoxy formamide Compound 10 (5.0 g, 12.9 mmol) in benzene (129 mL, 0.1 M) was added Co(acac)$_2$ (663 mg, 2.58 mmol, 0.2 equiv.) and TBAA (19.0 g, 64.6 mmol, 5.0 equiv.). The reaction mixture was stirred vigorously in a sealed flask that had been immersed in an oil bath preheated to 90° C. for 24 hours. The reaction mixture was then permitted to cool to ambient temperature and diluted with EtOAc (300 mL), washed with 1 M aq. HCl (100 mL), twice with sat. aq. NaHCO$_3$ (2×100 mL), H$_2$O (100 mL), and sat. aq. NaCl (100 mL), dried over MgSO$_4$, and concentrated in vacuo. The residue so obtained was purified by flash column chromatography (silica gel, CH$_2$Cl$_2$:acetone 5:1) furnishing 1.8 g of recovered Compound 10 and 2.8 g (48%, 76% brsm) of acetoxy hydroxy formamide Compound 11 as off-white free flowing micro-crystals, in addition to: $R_f$=0.44 (1:1 acetone:CH$_2$Cl$_2$); $[\alpha]_D$=+54.7° (c 0.51, CH$_2$Cl$_2$); IR (neat) $\nu_{max}$=3391, 2946, 1734, 1654, 1376, 1238, 1167, 1101, 1032 cm$^{-1}$; $^1$H NMR (600 MHz, CDCl$_3$) δ 8.09 (s, 1H), 5.72 (d, J=9.0 Hz, 1H), 5.64 (d, J=3.6 Hz, 1H), 5.37 (d, J=4.8 Hz, 1H), 4.50 (bs, 1H), 4.00 (bs, 1H), 3.94-3.88 (m, 2H), 3.85-3.78 (m, 2H), 3.45 (bs, 1H), 2.49 (d, J=12.0 Hz, 1H), 2.38-2.33 (m, 1H), 2.27 (d, J=10.8 Hz, 1H), 2.19-2.14 (m, 1H), 2.04-2.01 (m, 4H), 1.94-1.90 (m, 2H), 1.93 (s, 3H), 1.84-1.80 (m, 1H), 1.46 (s, 3H), 1.38-1.35 (m, 1H), 1.14-1.08 (m, 1H), 0.80 (s, 3H); $^{13}$C NMR (150 MHz, CDCl$_3$) δ 210.2, 169.0, 160.2, 144.6, 117.6, 116.2, 75.2, 68.7, 65.3, 64.5, 57.5, 49.3, 49.2 (2 C), 46.9, 39.4, 36.5, 34.3, 32.1, 32.0, 22.2, 21.0, 19.5, 14.9; HRMS (ESI-TOF) calcd for C$_{24}$H$_{33}$NO$_7$ [M+H]$^+$: 448.2330; found: 448.2329.

To a solution of acetoxy hydroxy formamide Compound 11 (870 mg, 1.94 mmol) in THF (19.0 mL, 0.102 M) and CH(OMe)$_3$ (6 mL, approximately ⅓ v/v relative to THF) was added Co(acac)$_2$ (100 mg, 0.389 mmol, 0.20 equiv) and PhSiH$_3$ (0.52 mL, 4.21 mmol, 2.17 equiv). The reaction mixture was saturated with O$_2$ by bubbling O$_2$ through the stirred solution for 30 minutes, and the stirring was continued under an O$_2$ atmosphere (no bubbling) at ambient temperature for approximately 12 hours. Then, p-TsOH.H$_2$O (1.08 g, 5.68 mmol, 2.92 equiv) was added.

Once the intermediate acetoxy diol was consumed as judged by TLC analysis, MeOH (20 mL) was added followed by K$_2$CO$_3$ (1.31 g, 9.48 mmol, 4.88 equiv). The reaction was stirred at ambient temperature for 6 hours. The reaction was then diluted with EtOAc (100 mL), washed with 1 M aq. HCl (20 mL), sat. aq. NaHCO$_3$ (30 mL), H$_2$O (20 mL), and sat. aq. NaCl (20 mL), dried over MgSO$_4$, and concentrated in vacuo. The residue so obtained was purified by flash column chromatography (silica gel, CH$_2$Cl$_2$:acetone 5:1) furnishing 534 mg (63%) orthoamide alcohol Compound 12 as a white foam: $R_f$=0.20 (20% acetone:CH$_2$Cl$_2$); $[\alpha]_D$=+33.6° (c 0.69, CH$_2$Cl$_2$); IR (neat) $\nu_{max}$=3428, 2940, 1666, 1433, 1173, 1110, 1079, 1051, 1006, 964 cm$^{-1}$; $^1$H NMR (600 MHz, CDCl$_3$) δ 8.13 (s, 1H), 5.74 (s, 1H), 4.74 (d, J=3.0 Hz, 1H), 4.57 (s, 1H), 4.15-4.13 (m, 2H), 3.93-3.86 (m, 2H), 3.83-3.78 (m, 2H), 3.20 (d, J=11.4 Hz, 1H), 2.69 (d, J=12.6 Hz, 1H), 2.37 (dd, J=13.8, 1.8 Hz, 1H), 2.17-2.12 (m, 1H), 2.02 (d, J=12.6 Hz, 1H), 2.03-1.98 (m, 1H), 1.93-1.86 (m, 2H), 1.82-1.79 (m, 1H), 1.61-1.50 (m, 4H), 1.36 (s, 3H), 1.35-1.29 (m, 2H), 0.78 (s, 3H); $^{13}$C NMR (150 MHz, CDCl$_3$) δ 213.0, 157.4, 117.6, 96.2, 76.8, 74.8, 68.4, 65.3, 64.5, 53.2, 49.8, 49.4, 48.7, 46.9, 39.1, 35.2, 34.1, 31.7, 29.6, 24.8, 22.0, 15.0, 14.8; HRMS (ESI-TOF) calcd for C$_{23}$H$_{31}$NO$_7$ [M+H]$^+$: 434.2173; found: 434.2185.

Dibromide Compound SI-3:

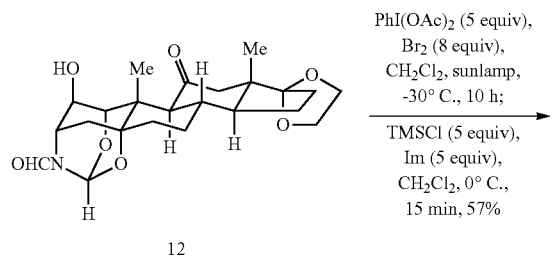

Bromocyclopropane Compound 13:

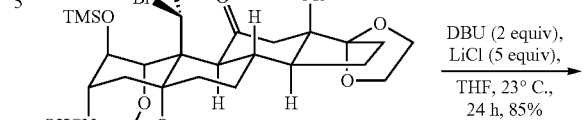

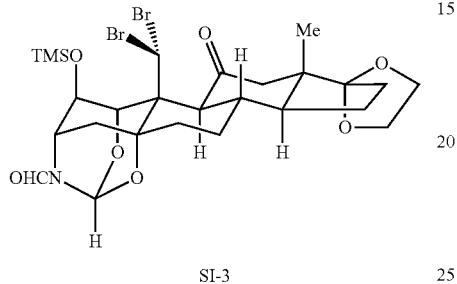

SI-3

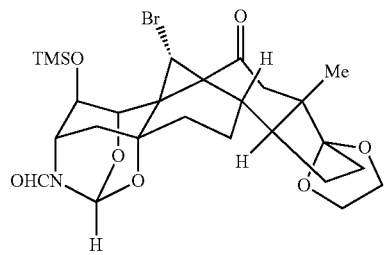

13

Orthoamide alcohol Compound 12 (1.01 g, 2.32 mmol) and PhI(OAc)$_2$ (3.74 g, 11.6 mmol, 5 equiv) were dissolved in CH$_2$Cl$_2$ (23 mL, 0.1 M) at room temperature under Ar. After cooling to −30° C., Br$_2$ (954 μL, 18.6 mmol, 8 equiv) was added. The temperature was maintained between −30 and −36° C. with sunlamp irradiation (75 W, 18 inches above surface of cooling bath) for 10 hours. Irradiation was then halted, the reaction was diluted with ice-cold CH$_2$Cl$_2$ (200 mL), and the crude mixture was shaken with 10% aq. Na$_2$S$_2$O$_3$ (100 mL) until colorless. The aqueous layer was back-extracted twice with CH$_2$Cl$_2$ (2×100 mL), dried over MgSO$_4$, filtered, and concentrated in vacuo at 5° C. to about 40 mL. At zero ° C., imidazole (0.79 g, 11.7 mmol, 5 equiv) and TMSCl (1.5 mL, 11.7 mmol, 5 equiv) were added. After 10 minutes, the reaction was diluted with EtOAc (200 mL), washed with water (20 mL), followed by sat. aq. NaHCO$_3$ (20 mL), and then sat. aq. NaCl (10 mL), dried over MgSO$_4$, filtered, and concentrated in vacuo. Purification by flash column chromatography (silica gel, 40% EtOAc:hexanes) afforded dibromide Compound SI-3 (877 mg, 57%) as a white foam: R$_f$=0.18 (1:9 EtOAc:CH$_2$Cl$_2$); IR (neat) ν$_{max}$=3354, 2957, 2882, 1686, 1424, 1254, 1173, 1115, 1083, 1042, 873, 846, 732, 723 cm$^{-1}$; $^1$H NMR (600 MHz, CDCl$_3$) δ 8.17 (s, 1H), 7.59 (s, 1H), 5.80 (s, 1H), 5.70 (dd, J=3.6, 1.2 Hz, 1H), 4.46 (bs, 1H), 4.16 (dd, J=3.0, 1.8 Hz, 1H), 3.96-3.91 (m, 2H), 3.88-3.81 (m, 2H), 3.35 (d, J=11.4 Hz, 1H), 3.30-3.24 (m, 1H), 2.98-2.93 (m, 1H), 2.64 (d, J=16.8 Hz, 1H), 2.31 (d, J=17.4 Hz, 1H), 2.24 (dd, J=14.7, 1.5 Hz, 1H), 2.06-2.02 (m, 2H), 1.92 (dd, J=9.3, 5.1 Hz, 1H), 1.89-1.80 (m, 2H), 1.76-1.71 (m, 1H), 1.58 (dd, J=12.0, 6.0 Hz, 1H), 1.47-1.41 (m, 1H), 1.35 (dd, J=15.3, 5.1 Hz, 1H), 1.21 (s, 3H), 0.24 (s, 9H); $^{13}$C NMR (150 MHz, CDCl$_3$) δ 211.0, 157.3, 118.2, 95.5, 78.4, 72.9, 69.4, 65.3, 64.5, 53.2 (2 C), 48.7 (2 C), 46.9, 46.3, 41.3, 33.7, 32.4 (2 C), 29.3, 25.9, 22.7, 16.7, −0.4 (3 C); HRMS (ESI-TOF) calcd for C$_{26}$H$_{37}$Br$_2$NO$_7$Si [M+H]$^+$: 662.0779; found: 662.0774.

Dibromide Compound SI-3 (496 mg, 0.75 mmol) was dissolved in THF (15 mL, 0.05 M) and flame-dried LiCl (158 mg, 3.75 mmol, 5 equiv) was added, followed by dry DBU (224 μL, 1.5 mmol, 2 equiv). The reaction mixture was stirred for 24 hours, at which point it was diluted with EtOAc (50 mL), washed twice with water (10 mL), and once with sat. aq. NaCl (10 mL). The aqueous layer was extracted twice with CH$_2$Cl$_2$ (2×30 mL); these portions were added to the EtOAc-containing organic phase, which was dried with MgSO$_4$, filtered, and concentrated in vacuo. Flash column chromatography (silica gel, 30% EtOAc:hexanes) afforded bromocylopropane 13 (370 mg, 85%) as a colorless foam: R$_f$=0.36 (1:1 EtOAc:hexanes); [α]$_D$=+10.0° (c 0.50, CH$_2$Cl$_2$); IR (neat) ν$_{max}$=2957, 2882, 1738, 1684, 1425, 1252, 1117, 1032, 1012, 880, 844 cm$^{-1}$; $^1$H NMR (600 MHz, CDCl$_3$) δ 8.18 (s, 1H), 5.80 (s, 1H), 5.16 (d, J=3.6 Hz, 1H), 4.47 (s, 1H), 4.11 (t, J=3.3 Hz, 1H), 3.93-3.81 (m, 4H), 3.33 (s, 1H), 2.76 (d, J=17.4 Hz, 1H), 2.27 (d, J=18.0 Hz, 1H), 2.04-2.00 (m, 2H), 1.92-1.89 (m, 3H), 1.77 (dd, J=13.2, 3.0 Hz, 1H), 1.62-1.55 (m, 2H), 1.50-1.43 (m, 2H), 1.35-1.28 (m, 2H), 0.99 (s, 3H), 0.17 (s, 9H); $^{13}$C NMR (150 MHz, CDCl$_3$) δ 205.9, 157.6, 118.1, 96.6, 72.2, 69.3, 67.5, 65.3, 64.5, 49.3, 48.9, 46.8, 44.9, 40.8, 40.4, 39.3, 35.4, 33.6, 32.8, 31.9, 24.2, 21.0, 15.8, −0.2 (3 C); HRMS (ESI-TOF) calcd for C$_{26}$H$_{36}$BrNO$_7$Si [M+H]$^+$: 582.1517; found: 582.1518.

α-Bromo-β,γ-enone Compound 14:

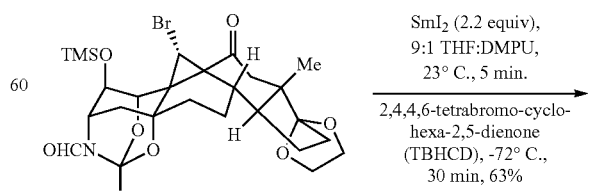

13

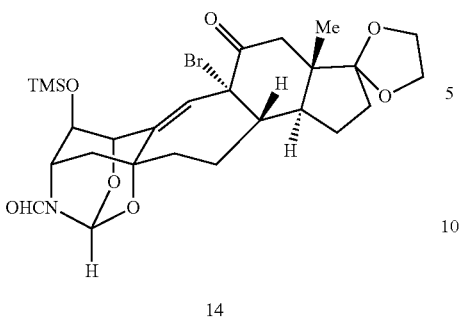

14

Bromocyclopropane Compound 13 (109 mg, 0.19 mmol) was dissolved in THF (3.3 mL, 0.05 M) under Ar and freshly distilled DMPU (0.37 mL) was added. The solution was bubbled with Ar for 10 minutes, after which SmI$_2$ (4.1 mL, 0.41 mmol, 2.2 equiv, 0.1 M in THF) was quickly added. After 2 minutes, the reaction was cooled to −72° C. and 2,4,4,6-tetrabromo-2,5-cyclohexadienone (TBCHD, 1.9 mL, 0.37 mmol, 2 equiv, 0.2 M in CH$_2$Cl$_2$) was added; the reaction was stirred at this temperature for 30 minutes, after which it was quenched with sat. aq. NaHCO$_3$ solution (10 mL). After warming to ambient temperature, the reaction was diluted with EtOAc (10 mL) and washed with sat. aq. Na$_2$S$_2$O$_3$ (20 mL). The aqueous layer was extracted four times with EtOAc (4×10 mL) and the combined organic portions were dried over MgSO$_4$, filtered, and concentrated in vacuo. Chromatography on silica (1:3 EtOAc:hexanes) furnished α-bromo-β,γ-enone Compound 14 as a white foam (yield was calculated after subsequent step): R$_f$=0.46 (1:1 EtOAc:hexanes); IR (neat) $v_{max}$=2959, 1686, 1426, 1176, 1120, 1034, 882, 846 cm$^{-1}$; $^1$H NMR (600 MHz, C$_6$D$_6$) δ 7.78 (s, 1H), 7.00 (s, 1H), 5.47 (s, 1H), 4.76 (bs, 1H), 4.13 (d, J=3.0 Hz, 1H), 4.05 (bt, J=3.3 Hz, 1H), 3.60 (d, J=13.8 Hz, 1H), 3.39-3.32 (m, 2H), 3.25-3.17 (m, 2H), 2.96-2.92 (m, 1H), 2.38-2.33 (m, 1H), 2.28 (d, J=13.2 Hz, 1H), 2.06 (dd, J=13.2, 2.4 Hz, 1H), 1.90-1.84 (m, 1H), 1.82-1.77 (m, 1H), 1.63-1.60 (m, 2H), 1.49-1.54 (m, 3H), 1.42-1.36 (m, 1H), 0.95-0.92 (m, 1H), 0.75 (s, 3H), −0.11 (s, 9H); $^{13}$C NMR (150 MHz, C$_6$D$_6$) δ 199.2, 157.6, 141.1, 125.2, 117.7, 96.4, 79.6, 77.1, 68.6, 65.3, 64.6, 63.9, 47.6, 47.4, 45.8, 43.8, 43.2, 33.8, 33.4 (2 C), 25.3, 22.4, 14.9, −0.3; HRMS (ESI-TOF) calcd for C$_{26}$H$_{36}$BrNO$_7$Si [M+H]$^+$: 582.1517; found: 582.1521.

Dienone Compound 16:

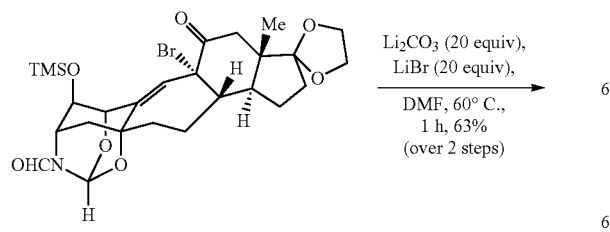

14

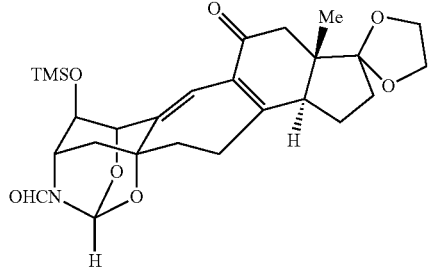

16

α-Bromo-β,γ-enone Compound 14 (108 mg crude from previous reaction, stoichiometry is based on 14) was dissolved in DMF (18 mL, 0.01 M) and to this solution were added LiBr (314 mg, 3.7 mmol, 20 equiv) and Li$_2$CO$_3$ (274 mg, 3.7 mmol, 20 equiv). The reaction mixture was stirred at 60° C. for 1 hour, at which point it was permitted to cool to ambient temperature, diluted with EtOAc (30 mL) and washed with sat. aq. NaHCO$_3$ solution (30 mL). The aqueous layer was extracted four times (4×20 ml) with EtOAc. The organic portions were combined, dried with MgSO$_4$, filtered, and concentrated in vacuo. Flash column chromatography (silica gel, 20% EtOAc:hexanes) afforded dienone Compound 16 (59 mg, 63%) as a white solid: R$_f$=0.26 (1:1 EtOAc:hexanes); [α]$_D$=−10.2° (c 0.93, CH$_2$Cl$_2$), IR (neat) $v_{max}$=2953, 1678, 1426, 1253, 1128, 1081, 1038, 878, 846 cm$^{-1}$; $^1$H NMR (600 MHz, CDCl$_3$) δ 8.22 (s, 1H), 6.50 (s, 1H), 5.90 (s, 1H), 4.58 (s, 1H), 4.28 (dd, J=4.2, 1.8 Hz, 1H), 4.10 (t, J=3.6 Hz, 1H), 3.96-3.92 (m, 2H), 3.89-3.83 (m, 2H), 3.14 (dd, J=15.0, 7.5 Hz, 1H), 2.64 (d, J=16.2 Hz, 1H), 2.50 (dd, J=14.7, 11.1 Hz, 1H), 2.35 (d, J=16.8 Hz, 1H), 2.36-2.29 (m, 1H), 2.15-2.06 (m, 2H), 2.03-1.91 (m, 4H), 1.67-1.56 (m, 2H), 0.90 (s, 3H), 0.15 (s, 9H); $^{13}$C NMR (150 MHz, CDCl$_3$) δ 197.4, 163.5, 157.6, 135.5, 129.1, 119.9, 117.5, 96.9, 80.7, 77.6, 66.8, 65.5, 46.6, 48.0 (2 C), 47.0, 46.1, 38.5, 34.0, 33.3, 25.3, 22.3, 14.9, 0.1; HRMS (ESI-TOF) calcd for C$_{26}$H$_{35}$NO$_7$Si [M+H]$^+$: 502.2255; found: 502.2273.

Triacetate Compound 15:

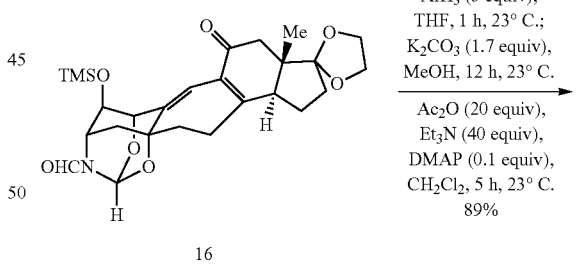

16

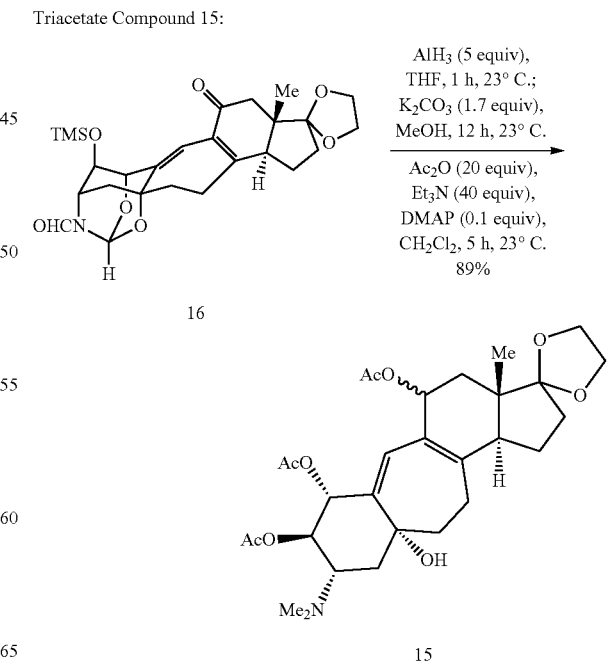

15

A freshly prepared solution of alane (0.84 mL, 0.419 mmol, 5 equiv, 0.5 M in THF) was added to dienone Compound 16 (42 mg, 0.083 mmol) in THF (1.6 mL, 0.1 M) at ambient temperature. After stirring vigorously for 1 hour, methanol (5.0 mL) was added dropwise, followed by $K_2CO_3$ (20 mg, 0.14 mmol, 1.7 equiv). This suspension was then stirred for 12 hours, at which point it was filtered through cotton and concentrated in vacuo. The resulting white residue was suspended in $CH_2Cl_2$ (1.7 mL, 0.05 M) followed by the addition of $Et_3N$ (0.23 mL, 1.7 mmol, 20 equiv), $Ac_2O$ (83 μL, 0.83 mmol, 10 equiv), and DMAP (1 mg, 0.008 mmol, 0.1 equiv). After 5 hours, the reaction mixture was diluted with $CH_2Cl_2$ (5.0 mL) and sat. aq. sodium potassium tartrate (1.0 mL). The organic phase was removed and the aqueous layer extracted two more times with $CH_2Cl_2$ (2×5.0 mL). Drying over $Na_2SO_4$, filtration, concentration in vacuo, and flash column chromatography (silica gel, 10% MeOH:EtOAc) yielded Compound 15 (42 mg, 92%, mixture of diastereomers) as a white solid.

Cortistatinone Compound 8:

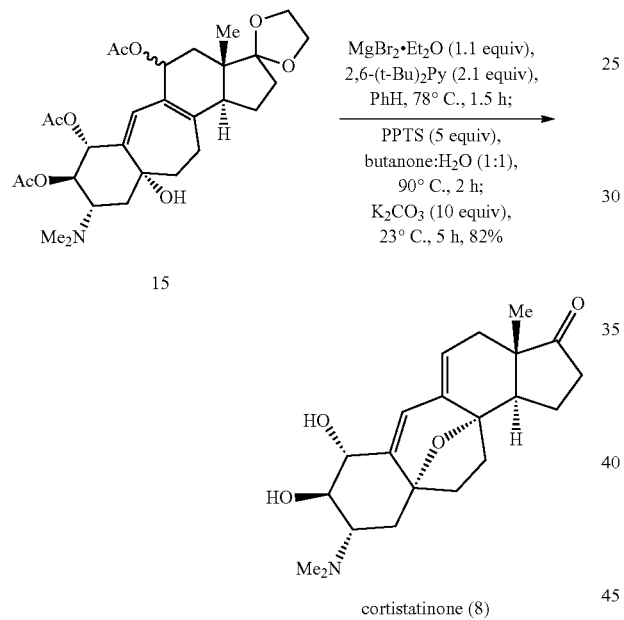

cortistatinone (8)

To a solution of triacetate Compound 15 (13 mg, 0.024 mmol) in PhH (4.7 mL, 0.005 M) was added 2,6-di-t-butylpyridine (10.7 μL, 0.047 mmol, 2 equiv) and $MgBr_2 \cdot Et_2O$ (6.7 mg, 0.026 mmol, 1.1 equiv; dissolved in 0.26 mL MeCN) and the reaction was warmed to 78° C. After 1.5 hours, the reaction mixture was cooled to ambient temperature and filtered through Celite, which was rinsed with two portions of EtOAc (2×2 mL). Concentration in vacuo delivered a yellow residue, which was immediately dissolved in butanone and water (1:1, 2.4 mL, 0.01 M) and heated at 90° C. with pyridinium p-toluenesulfonate (PPTS, 30 mg, 0.12 mmol, 5 equiv). After 2 hours, the reaction was cooled to ambient temperature and $K_2CO_3$ was added. After 5 hours, the reaction was concentrated in vacuo, and the residue was dissolved in $CH_2Cl_2$ (2 mL) and sat. aq. NaCl (1 mL) was added. The aqueous layer was extracted 5 times with $CH_2Cl_2$ (5×3 mL), and the combined organic phases were passed through a plug of $Na_2SO_4$, and concentrated in vacuo. The crude residue was purified using preparatory thin layer chromatography (reverse phase: C18, 0.25 mm, E. Merck, RP-18 $F_{254s}$; MeOH:$H_2O$:sat. aq. $NH_4OH$, 5:4:1), furnishing (+)-cortistatinone (Compound 8) (7 mg, 82%) as a white solid: $R_f$=0.17 (20% MeOH:EtOAc); $[\alpha]_D$=+148.0° (c 0.60, $CH_2Cl_2$); IR (neat) $\nu_{max}$=3393, 2933, 2356, 1734, 1456, 1072, 1018, 1002 cm$^{-1}$; $^1$H NMR (600 MHz, CDCl$_3$) δ 6.25 (d, J=1.9 Hz, 1H), 5.44 (dd, J=4.7, 2.7 Hz, 1H), 4.16 (d, J=10.9 Hz, 1H), 3.42 (t, J=9.8, Hz, 1H), 2.76 (bt, J=10.3 Hz, 1H), 2.56-2.49 (m, 2H), 2.44 (s, 6H), 2.37 (dd, J=12.7, 5.8 Hz, 1H), 2.27-2.18 (m, 4H), 2.15-2.10 (m, 1H), 1.97 (dd, J=12.4, 3.1 Hz, 1H), 1.91-1.79 (m, 3H), 1.72-1.67 (m, 1H), 0.91 (s, 3H); $^{13}$C NMR (150 MHz, CDCl$_3$) δ 220.3, 139.9, 139.4, 120.9, 119.5, 81.6, 79.4, 73.9, 73.0, 62.3, 47.8, 47.1, 40.0 (2 C), 39.7, 35.9, 33.9, 31.4, 29.4, 18.8, 16.9; HRMS (ESI-TOF) calcd for $C_{21}H_{29}NO_4$ [M+H]$^+$: 360.2169; found: 360.2174.

Alternative Synthesis of Cortistatinone Compound 8

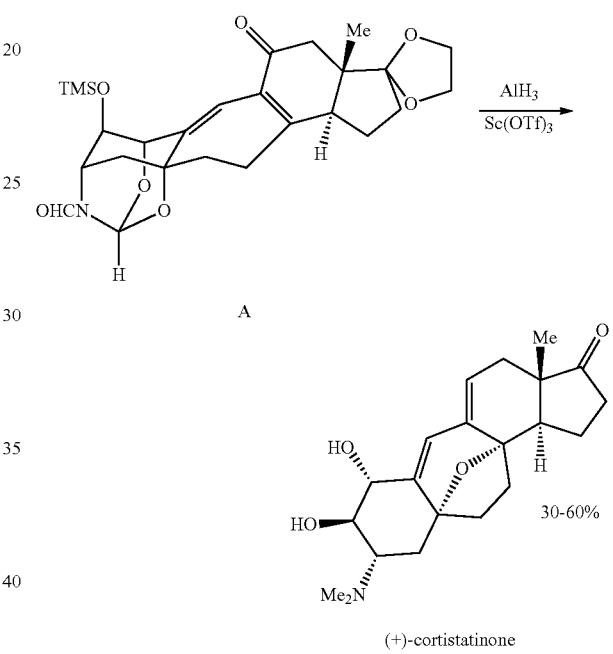

(+)-cortistatinone

A freshly prepared solution of alane (0.64 mL, 0.32 mmol, 5 equiv, 0.5 M in THF) was added to dienone compound A (32 mg, 0.064 mmol) in THF (1.2 mL, 0.05 M) at ambient temperature. After stirring vigorously for 1 hour to react most of compound A to form a tetraol and a gelatinous aluminum-containing reaction product, methanol (5.0 mL) was added dropwise, followed by $K_2CO_3$ (16 mg, 0.11 mmol, 1.7 equiv). This resulting suspension was then stirred for 12 hours, at which point the reaction mixture was diluted with $CH_2Cl_2$ (5.0 mL) and sat. aq. sodium potassium tartrate (5.0 mL) to precipitate the aluminum-containing gelatinous product that formed. The organic phase was removed and the aqueous layer extracted two more times with $CH_2Cl_2$ (2×5.0 mL) to separate the tetraol.

After drying over $Na_2SO_4$, filtration, concentration in vacuo, the tetraol residue was dissolved into benzene (12.8 mL, 0.005 M) and Sc(OTf)$_3$ (41 mg, 0.419 mmol, 1.5 equiv, dissolved in 0.5 mL MeCN) was added. The reaction mixture so formed was warmed to 40° C. After 1.5 hours, the reaction mixture was cooled to ambient temperature and filtered through Celite, which was rinsed with two portions of EtOAc (2×2 mL). Concentration in vacuo provided a yellow residue, which, after flash column chromatography (silica gel, 1%

Et$_3$N and 10% MeOH in EtOAc), yielded (+)-cortistatinone 8 (9.4 mg, 0.026 mmol, 41%) as a white foam.

Alternatively useful Lewis acids that can be used in place of Sc(OTf)$_3$ in the above reaction include Bi(OTf)$_3$, Bi(Cl)$_3$, Zn(OTf)$_2$, Y(OTf)$_3$, TFA, HCl, and acetic acid. Alternatively useful solvents that can be used with an alternative Lewis acid include THF, toluene, water, dichloromethane, and (trifluoromethyl)benzene [α,α,α-trifluorotoluene].

Vinyl iodide Compound SI-6:

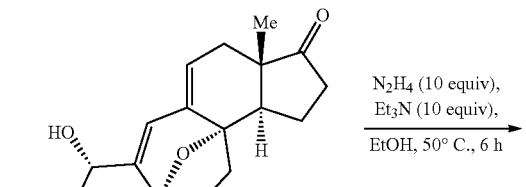

cortistatinone (8)

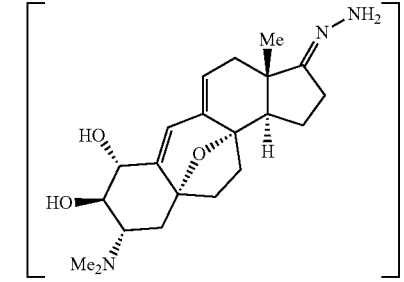

SI-5

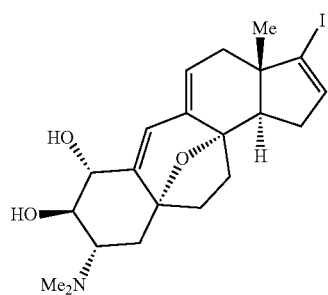

SI-6

To a solution of cortistatinone 8 (6.0 mg, 17 μmol) in absolute EtOH (300 μL, 0.06 M) were added hydrazine monohydrate (8.1 μL, 170 μmol, 10 equiv) and Et$_3$N (233 μL, 170 μmol, 10 equiv). The reaction was immersed in a preheated oil bath at 50° C. for 6 hours, after which the reaction was permitted to cool and the solvent removed in vacuo. The residue so obtained was dissolved in THF (300 μL, 0.06 M), and Et$_3$N (7 μL, 0.050 mmol, 3 equiv) was added. A stock solution of I$_2$ (8.6 mg, 33 μmol, 2 equiv) in THF (84.5 μL) was prepared and added dropwise to the reaction mixture; addition was halted when the iodine was not decolorized after 30 seconds. The reaction was then diluted with EtOAc (5 mL) and washed with sat. aq. Na$_2$S$_2$O$_3$ (5 mL). The aqueous layer was extracted four times with EtOAc (4×5 mL). The combined organic portions were washed with sat. aq. NaCl (10 mL), dried over MgSO$_4$, filtered, and concentrated in vacuo to furnish vinyl iodide Compound SI-6 that was carried forward directly without purification.

Vinylisoquinoline Compound 26:

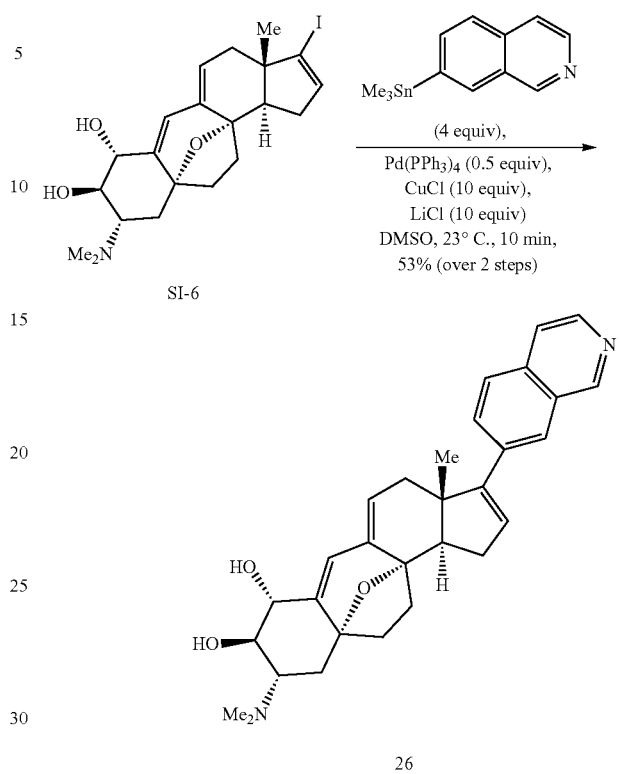

The residue from the previous reaction (Compound SI-6, yield assumed to be quantitative) was dissolved in DMSO (300 μL, 0.06 M. To this solution was added 7-trimethylstannylisoquinoline (20 mg, 68 μmol, 4 equiv), CuCl (15 mg, 170 μmol, 10 equiv), LiCl (7 mg, 170 μmol, 10 equiv) and Pd(PPh$_3$)$_4$ (10 mg, 85 μmol, 0.5 equiv). The reaction was degassed by bubbling argon through the solution for 10 minutes. A vessel containing the degassed solution was immersed in a preheated oil bath at 60° C. for 1 hour. The reaction was then diluted with EtOAc (5 mL) and washed with 5% aq. NH$_4$OH. The aqueous layer was extracted four times (4×5 ml) with EtOAc. The combined organic portions were washed with sat. aq. NaCl (5 mL), dried over MgSO$_4$, filtered, and concentrated in vacuo. The residue so obtained was purified by PTLC (NH$_3$ deactivation; 10% MeOH:CH$_2$Cl$_2$) furnishing vinylisoquinoline Compound 26 (4 mg, 53% from cortistatinone Compound 8) as a yellow foam, which exhibited atropisomerism by NMR (the major isomer is recorded): OR not recorded due to aptropisomerism; $^1$H NMR (CDCl$_3$, 600 MHz): 9.22 (bs, 1H), 8.48 (bs, 1H), 7.92 (s, 1H), 7.79 (dd, J=8.6, 1.6 Hz, 1H), 7.75 (d, J=8.6 Hz, 1H), 7.61 (d, J=5.5 Hz, 1H), 6.29 (d, J=1.9 Hz, 1H), 6.24 (as, 1H), 5.57-5.52 (m, 1H), 4.13 (d, J=9.0 Hz, 1H), 3.37 (at, J=3.37, 1H), 2.75 (dd, J=11.2, 6.9 Hz, 1H), 2.61 (dd, J=9.0 Hz, 5.8 Hz, 1H), 2.56-2.48 (m, 3H), 2.47-2.38 (m, 2H), 2.35 (s, 6H), 2.23 (t, J=10.1 Hz, 1H), 2.05-1.96 (m, 2H), 1.96-1.87 (m, 1H), 1.76-1.68 (m, 1H), 1.15 (s, 3H); $^{13}$C NMR (150 MHz, CDCl$_3$) δ 152.5, 150.4, 142.8, 140.0, 139.4, 135.3, 134.8, 134.3, 130.0, 128.4, 126.4, 123.9, 121.8, 120.2, 119.4, 81.2, 79.3, 74.1, 73.5, 62.3, 53.3, 47.7, 40.0 (2 C), 39.6, 38.2, 31.0, 29.3, 28.6, 19.3; HRMS (ESI-TOF) calcd for C$_{30}$H$_{34}$N$_2$O$_3$ [M+H]$^+$: 471.2642; found: 471.2656.

(+)-Cortistatin A Compound 1:

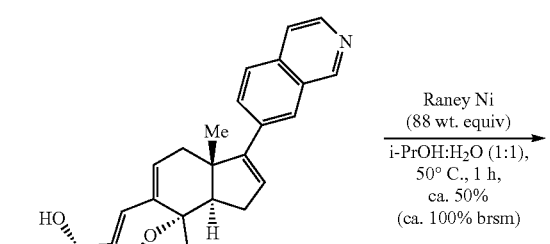

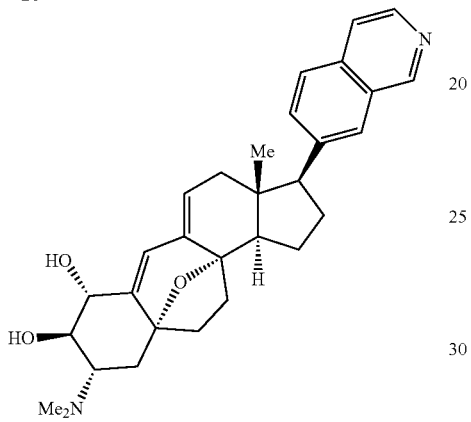

For this procedure, Raney nickel (1.0 g) was washed with $H_2O$ (3×5 mL), sat. aq. Rochelle's salt (3×5 mL), $H_2O$ (5×5 mL), MeOH (3×5 mL), and $H_2O$ again (3×5 mL, all supernatants were removed with pipette) after which it was stored under $H_2O$ (10 mL). To alkenylisoquinoline Compound 26 (2.0 mg, 0.004 mmol) in i-PrOH (3 mL) and $H_2O$ (3 mL), was added the washed Raney nickel (176 mg, 88 wt. equiv, which includes water). The heterogeneous reaction was warmed to 50° C. while stirring vigorously for 1 hour, at which point the reaction had progressed to approximately 50% conversion, as judged by LCMS. Removal of the supernatant, followed by washing of the Raney nickel catalyst with 1:1 MeOH:EtOAc (4 mL), and concentration of the combined filtrates yielded a colorless residue, which was purified by HPLC (Eclipse XDB-C8 column, 9.4 mm×25 cm; gradient=1%→30% $MeCN:H_2O$ over 30 min), yielding recovered Compound 26 (ca. 1 mg) and (+)-cortistatin A Compound 1 (ca. 1 mg, ca. 50%; ca. 100% brsm) as a white solid: $[\alpha]_D$=+31.4 (c 0.035, MeOH) [lit: $[\alpha]_D$=+30.1 (c 0.56, MeOH)]; $^1H$ NMR ($CDCl_3$, 600 MHz): 9.22 (1H), 8.49 (d, J=5.3 Hz, 1H), 7.79 (s, 1H), 7.76 (d, J=8.3 Hz, 1H), 7.63 (d, J=5.3 Hz, 1H), 7.59 (d, J=8.5 Hz, 1H), 6.25 (d, J=1.6 Hz, 1H), 5.44 (d, J=3.0 Hz, 1H), 4.09 (d, J=9.5 Hz, 1H), 3.33 (t, J=9.8 Hz, 1H), 3.15 (t, J=9.9 Hz, 1H), 2.51 (dd, J=11.3, 8.6, 1H), 2.46-2.42 (m, 1H), 2.39-2.33 (m, 2H), 2.30 (s, 6H), 2.28-2.26 (m, 2H), 2.23-2.16 (m, 2H), 2.07-2.01 (m, 1H), 1.97 (dd, J=17.4, 5.2 Hz, 1H), 1.93 (dd, J=13.3, 3.3 Hz, 1H), 1.90-1.83 (m, 2H), 1.78 (add, 12.9, 8.7, 8.2 Hz, 1H), $H_2O$ peak covers proton at 1.66 (1H), 0.54 (s, 3H); $^{13}C$ NMR (150 MHz, $CDCl_3$) δ 152.3, 142.5, 140.0, 139.7, 139.5, 134.7, 132.0, 128.5, 126.3, 125.8, 121.5, 120.1, 119.5, 81.9, 79.5, 74.1, 73.7, 62.2, 56.9, 51.6, 44.8, 40.1 (2C), 40.0, 39.7, 30.6, 29.1, 26.4, 20.5, 15.2; for NMR data comparisons, see Tables 1 and 2 (vide infra); HRMS (ESI-TOF) calcd for $C_{30}H_{36}N_2O_3$ $[M+H]^+$: 473.2799; found: 473.2807.

TABLE 1

$^1H$ NMR data comparison between synthetic (+)-cortistatin A (1) and natural (+)-cortistatin A

| Synthetic 1 ($CDCl_3$, 600 MHz) | Natural 1 ($CDCl_3$, 600 MHz) |
|---|---|
| 0.54 | 0.54 |
| $H_2O$ peak | 1.66 |
| 1.78 | 1.78 |
| 1.84* | 1.84 |
| 1.88* | 1.89 |
| 1.93 | 1.93 |
| 1.97* | 1.97 |
| 2.04* | 2.05 |
| 2.17* | 2.19 |
| 2.22* | 2.21 |
| 2.27* | 2.28 |
| 2.30 | 2.30 |
| 2.35* | 2.35 |
| 2.38* | 2.38 |
| 2.44* | 2.43 |
| 2.51 | 2.51 |
| 3.15 | 3.15 |
| 3.33 | 3.33 |
| 4.09 | 4.09 |
| 5.44 | 5.44 |
| 6.25 | 6.25 |
| 7.59 | 7.59 |
| 7.63 | 7.63 |
| 7.76 | 7.76 |
| 7.79 | 7.78 |
| 8.49 | 8.49 |
| 9.22 | 9.22 |

*Calculated as center of observed multiplet

TABLE 2

$^{13}C$ NMR data comparison between synthetic (+)-cortistatin A (1) and natural (+)-cortistatin A

| Synthetic 1 ($CDCl_3$, 150 MHz) | Natural 1 ($CDCl_3$, 150 MHz) |
|---|---|
| 15.2 | 15.2 |
| 20.5 | 20.5 |
| 26.4 | 26.4 |
| 29.1 | 29.1 |
| 30.6 | 30.5 |
| 39.7 | 39.7 |
| 40.0 | 40.0 |
| 40.1 | 40.1 |
| 44.8 | 44.8 |
| 51.6 | 51.6 |
| 56.9 | 56.9 |
| 62.2 | 62.2 |
| 73.7 | 73.7 |
| 74.1 | 74.1 |
| 79.5 | 79.5 |
| 81.9 | 81.9 |
| 119.5 | 119.5 |
| 120.1 | 120.1 |
| 121.5 | 121.5 |
| 125.8 | 125.8 |
| 126.3 | 126.3 |
| 128.5 | 128.5 |
| 132.0 | 132.0 |
| 134.7 | 134.7 |
| 139.5 | 139.5 |
| 139.7 | 139.8 |
| 140.0 | 139.9 |
| 142.5 | 142.5 |
| 152.3 | 152.3 |

7-Trimethylstannylisoquinoline:

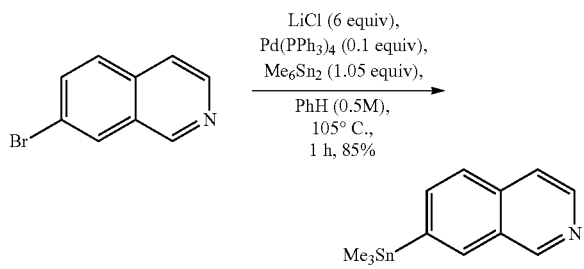

To a solution of 7-bromoisoquinoline (800 mg, 3.9 mmol) in PhH (7.8 mL, 0.5 M) was added LiCl (982 mg, 23.2 mmol, 6 equiv), Pd(PPh$_3$)$_4$ (446 mg, 0.39 mmol, 0.1 equiv) and hexamethylditin (1.3 g, 4.0 mmol, 1.05 equiv). The solution within its reaction vessel was bubbled with Ar while sonicating for 10 minutes. The reaction vessel was then immersed in a preheated oil bath at 105° C. After 1 hour, the reaction was permitted to cool to ambient temperature and diluted with EtOAc (10 mL) and filtered through Celite that was rinsed with two portions of EtOAc (2×5 mL). The organic portion was washed with NaHCO$_3$ (30 mL) and sat. aq. NaCl (30 mL), dried over MgSO$_4$, filtered, and concentrated in vacuo. Flash column chromatograph (silica gel, 306 Et$_2$O:hexanes) afforded 7-trimethylstannylisoquinoline (970 mg, 85% as a white solid: R$_f$=0.33 (1:1 Et$_2$O:hexanes); IR (neat) $v_{max}$=3041, 2982, 2909, 1616, 1374, 1336, 1063, 1028, 847, 775, 760, 734 cm$^{-1}$; $^1$H NMR (500 MHz, CDCl$_3$) δ 9.24 (s, 1H), 8.50 (d, 1H, J=5.7 Hz), 8.09 (t, J=24.0 Hz, 1H), 7.78 (dd, J=17.0, 8.0 Hz, 2H), 7.61 (d, J=5.7 Hz, 1H), 0.38 (t, J=26.6 Hz, 9 H); $^{13}$C NMR (125 MHz, CDCl$_3$) δ 152.3, 142.9, 142.2, 136.8, 135.6, 128.3, 125.4, 120.3, −9.4, 1 C missing; HRMS (ESI-TOF) calcd for C$_{12}$H$_{15}$NSn [M+H]$^+$: 294.0299; found: 294.0301.

Isoquinolinol Compound 28:

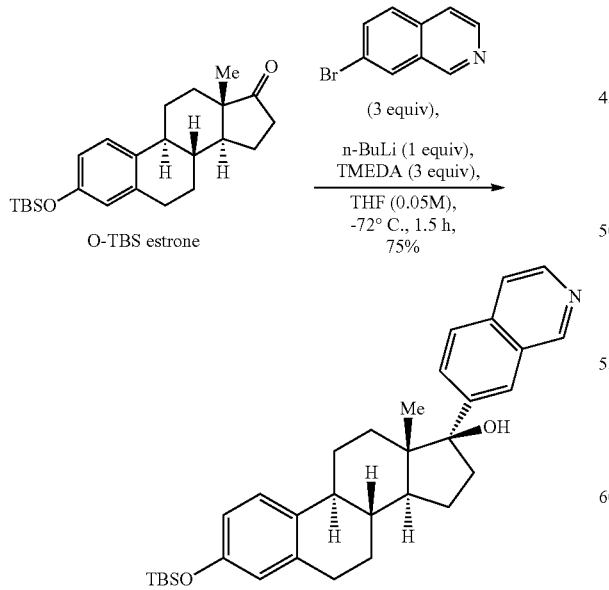

7-Bromoisoquinoline (40 mg, 0.193 mmol, 3 equiv) was dissolved in THF (1 mL, 0.19 M) and cooled down to −72° C. (dry ice-isopropanol bath), after which n-BuLi (88 µL, 2.3 M, 0.19 mmol, 3 equiv) was added dropwise. After 40 minutes, TMEDA (88 µL, 0.58 mmol, 9 equiv) was added into the solution. After 10 minutes, O-TBS-estrone (25 mg, 0.065 mmol, 1 equiv) in THF (0.3 mL, 0.22 M in THF) was added dropwise into the reaction solution. After 40 minutes, the reaction was quenched by the addition of sat. aq. NaHCO$_3$ (5 mL). The aqueous layer was extracted four times (4×10 mL) with EtOAc, washed with sat. aq. NaCl (20 mL), dried over MgSO$_4$, filtered, and concentrated in vacuo. Flash column chromatography (silica gel, 30% EtOAc:hexanes) afforded isoquinolinol Compound 28 (25 mg, 74%) as a yellow foam: R$_f$=0.31 (1:1 EtOAc:DCM); [α]$_D$=+16.9° (c 0.54, CH$_2$Cl$_2$); IR (neat) $v_{max}$=3210, 1496, 1285, 1251, 837 cm$^{-1}$; $^1$H NMR (500 MHz, CDCl$_3$) δ 9.28 (s, 1H), 8.51 (d, J=4.8 Hz, 1H), 7.88 (d, J=7.8 Hz, 2H), 7.79 (d, J=8.9 Hz, 1H), 7.65 (d, J=5.6 Hz, 1H), 6.95 (d, J=8.3 Hz, 1H), 6.55-6.50 (m, 2H), 2.87-2.73 (m, 2H), 2.59 (ddd, J=5.1, 9.8, 14.8 Hz, 1H), 2.25 (ddd, J=4.4, 12.5, 17.1 Hz, 1H), 2.10-2.00 (m, 2H), 1.96-1.91 (m, 1H), 1.79 (td, J=4.0, 11.2 Hz, 1H), 1.75-1.65 (m, 2H), 1.50 (dddd, J=2.2, 10.8, 12.7, 21.6 Hz, 1H), 1.47-1.32 (m, 1H), 1.33-1.22 (m, 2H), 1.15 (s, 3H), 0.95 (s, 9H), 0.57 (td, J=4.1, 12.8 Hz, 1H), 0.16 (s, 6H); $^{13}$C NMR (125 MHz, CDCl$_3$) δ 153.2, 152.8, 145.2, 142.9, 137.6, 134.6, 132.8, 130.8, 127.9, 125.9, 125.3, 125.2, 120.0, 119.8, 117.0, 86.1, 48.3, 47.4, 43.3, 39.5, 38.9, 33.7, 29.6, 27.4, 26.1, 25.7, 24.2, 18.1, 14.8; HRMS (ESI-TOF) calcd for C$_{33}$H$_{43}$NO$_2$Si [M+H]$^+$: 514.3136; found: 514.3140.

Alkenylisoquinoline Compound 27:

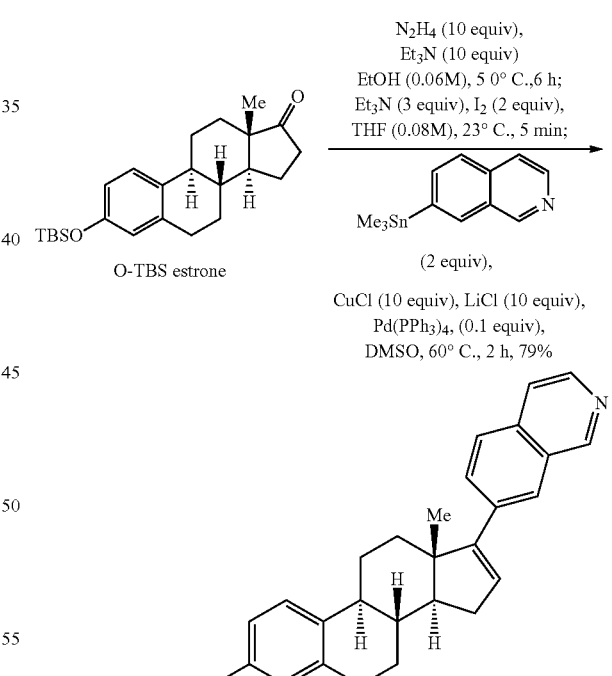

O-TBS-estrone (100 mg, 0.26 mmol) was dissolved in absolute EtOH (3 mL, 0.08 M), and hydrazine monohydrate (130 mg, 2.6 mmol, 10 equiv) and Et$_3$N (260 mg, 2.6 mmol, 10 equiv) were added into the solution. The reaction was heated to 50° C. for 6 hours, and then concentrated in vacuo. The residue was dissolved in THF (3 mL, 0.08 M) and Et$_3$N (107 µL, 0.78 mmol, 3 equiv) was added, followed by treatment with I$_2$ (132 mg, 0.52 mmol, 2 equiv, as a solution in 131

μL THF) until the color of iodine was not discharged after 30 seconds. The reaction was diluted with EtOAc (10 mL) and washed with sat. aq. $Na_2S_2O_3$ (20 mL). The aqueous layer was extracted with EtOAc (4×10 mL) and these portions were added to the organic layer, dried over $MgSO_4$, filtered, and concentrated in vacuo. The residue was dissolved into DMSO (2.6 mL, 0.1 M), and 7-trimethylstannyliso-quinoline (152 mg, 0.52 mmol, 2 equiv), CuCl (254 mg, 2.6 mmol, 10 equiv), LiCl (110 mg, 2.6 mmol, 10 equiv), and $Pd(PPh_3)_4$ (300 mg, 0.26 mmol, 0.1 equiv) were added. The solution was degassed for 10 minutes by sonication and bubbling with Ar within its reaction vessel, followed by immersion of the vessel for 2 hours in an oil bath preheated to 60° C. The reaction mixture was permitted to cool to ambient temperature, diluted with 10 mL EtOAc, and washed with 5% aq. $NH_4OH$. The aqueous layer was extracted four times with EtOAc (4×10 ml). The combined organic portions were washed with sat. aq. NaCl (20 mL), dried over $MgSO_4$, filtered, and concentrated in vacuo. Flash column chromatography (silica gel, 20% EtOAc:hexanes) afforded alkenylisoquinoline Compound 27 (103 mg, 79%) as a white solid: $R_f$=0.35 (1:3 EtOAc:hexanes); $[α]_D$=+22.5 (c 0.08, $CH_2Cl_2$); IR (neat) $ν_{max}$=2926, 2854, 1604, 1496, 1458, 1285, 1251, 1095, 954, 879, 841, 820, 782, 697 cm$^{-1}$; $^1$H NMR (600 MHz, $CDCl_3$) δ 9.23 (s, 1H), 8.48 (d, J=5.6 Hz, 1H), 7.95 (s, 1H), 7.77 (dd, J=15.8, 8.6 Hz, 1H), 7.61 (d, J=5.5 Hz, 1H), 7.13 (d, 8.4 Hz, 1H), 6.63 (dd, J=8.1, 2.0 Hz, 1H), 6.59 (s, 1H), 6.15 (s, 1H), 2.95-2.82 (m, 2H), 2.45-2.37 (m, 2H), 2.37-2.27 (m, 2H), 2.24-2.15 (1H), 2.03-1.94 (m, 1H), 1.86 (ddd, J=17.9, 11.4, 6.5 Hz, 1H), 1.77-1.67 (m, 2H), 1.54-1.46 (m, 1H), 1.37-1.27 (m, 1H), 1.16 (s, 3H), 0.98 (s, 9H), 0.20 (s, 6H); $^{13}$C NMR (150 MHz, $CDCl_3$) δ154.1, 153.3, 152.6, 142.7, 137.8, 136.2, 134.7, 133.1, 130.2, 129.1, 126.2, 125.8, 124.0, 120.0, 117.1, 56.9, 47.8, 44.1, 37.2, 35.6, 31.5, 27.7, 26.5, 25.7 (3 C), 18.2, 16.8, 1.0, −4.4 (2 C); HRMS (ESI-TOF) calcd for $C_{33}H_{41}NO_2Si$ $[M+H]^+$: 496.3030; found: 496.3036.

reaction vessel was immersed in an oil bath preheated to 115° C. and stirred vigorously for 80 minutes. The reaction then was permitted to cool to ambient temperature. The heterogeneous reaction mixture was taken up in portions and passed through Celite; this was facilitated by withdrawing portions of the suspension during vigorous stirring at ambient temperature to free the Raney nickel from the stir bar. The reaction vessel and Celite were rinsed repeatedly with EtOAc (approximately 10 mL total solvent) and the combined filtrates were concentrated in vacuo. Purification by flash column chromatography (silica gel, 3:1 hexanes:ethyl acetate) furnished starting material and desilylated starting material (neither was quantified) as well as Compound 29 (0.8 mg, 38% as a colorless thin oily film: $R_f$: 0.56 (1:1 EtOAc: hexanes); $[α]_D$=−2.0° (c 0.10, $CH_2Cl_2$); IR (neat) $ν_{max}$=2925, 2855, 1653, 1559, 1539, 1507, 1496, 1472, 1457, 1284, 1254, 947, 843 cm$^{-1}$; $^1$H NMR (600 MHz, $CDCl_3$) δ 9.22 (s, 1H), 8.47 (d, J=5.4 Hz, 1H), 7.80 (s, 1H), 7.75 (d, J=8.4 Hz, 1H), 7.62 (s, 1H), 7.61 (d, J=12.4 Hz, 1H), 7.11 (d, J=8.5, 1H), 6.60 (dd, J=8.5, 2.5 Hz, 1H), 6.56 (d, J=2.2 Hz, 1H), 2.98 (at, J=9.8 Hz, 1H), 2.90-2.78 (m, 2H), 2.34-2.24 (m, 3H), 2.15-2.07 (m, 1H), 2.02-1.94 (m, 2H), 1.73 (adt, J=12.9, 2.9 Hz, 1H), 1.57-1.38 (m, 6H), 0.97 (s, 9H), 0.54 (s, 3H), 0.18 (s, 6H); $^{13}$C NMR (150 MHz, $CDCl_3$) δ 153.3, 152.3, 142.3, 140.7, 137.8, 134.6, 133.1, 132.4, 128.6, 126.1, 126.0, 125.5, 120.1, 120.0, 117.1, 57.2, 55.3, 45.1, 44.0, 39.2, 37.8, 29.7, 27.8, 26.3, 26.2, 25.7 (3 C), 24.3, 18.2, 12.9, −4.4 (2 C); HRMS (ESI-TOF) calcd for $C_{33}H_{43}NOSi$ $[M+H]^+$: 498.3187; found: 498.3195.

17-α-isoquinoline estrone Compound 30:

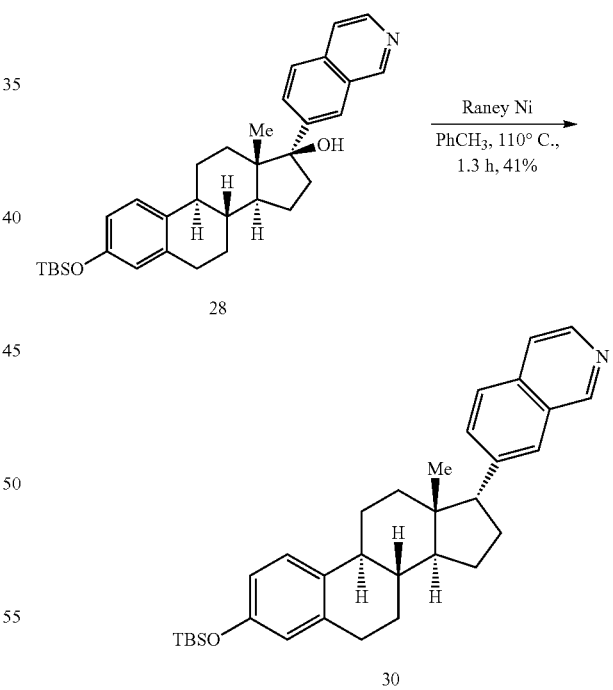

17-β-isoquinoline estrone Compound 29:

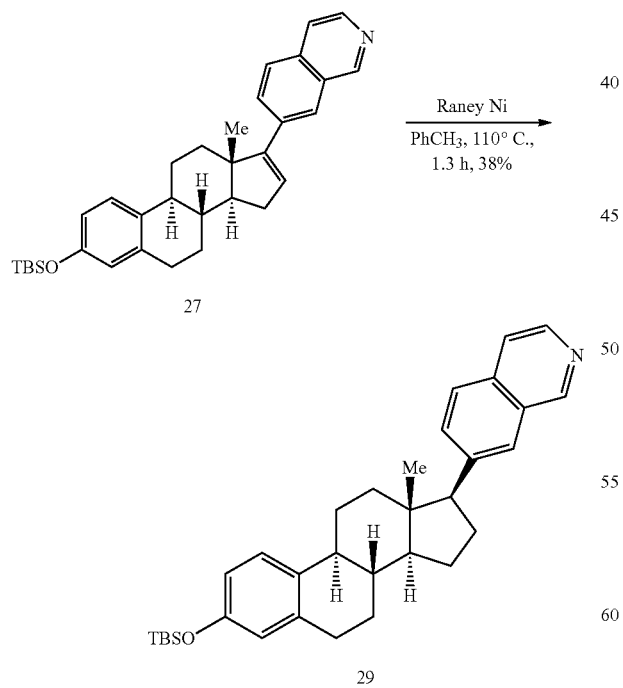

To a solution of Compound 27 (2.1 mg, 0.002 mmol) in toluene (0.5 mL) was added Raney nickel (50 mg, 24 wt. equiv; used without washing, as in Compounds 26→1). The To a solution of isoquinolinol Compound 28 (7.5 mg, 0.0145 mmol) in toluene (1 mL) was added Raney Ni (ca. 90 mg of slurry directly from the reagent bottle, 12 wt. equiv). The reaction vessel was immersed in an oil bath preheated to 115° C. and stirred vigorously. After 80 minutes, the reaction was permitted to cool to ambient temperature. The heterogeneous mixture was taken up in a pipette in portions and passed through Celite; this was facilitated by withdrawing portions of the suspension during vigorous stirring at ambient temperature to free the Raney nickel from the stir bar. The reaction vessel and Celite were rinsed repeatedly with EtOAc (approximately 5 mL total volume) and the combined filtrates were concentrated in vacuo. Purification by PTLC (silica gel, 1:1 hexanes:ethyl acetate) furnished starting material and desilylated starting material (neither was quantified) as well as Compound 30 as a 4.3:1 mixture of diastereomers (3.0 mg, 41%) as a thin film: $R_f$=0.39 (silica gel, 3:1 hexanes:ethyl acetate); $^1$H NMR (500 MHz, CDCl$_3$) δ 9.25 (bs, 1H), 8.48 (bs, 1H), 7.74 (d, J=14.4 Hz, 1H), 7.67 (s, 1H), 7.58-7.54 (m, 2H), 7.51 (d, J=8.8 Hz, 1H), 6.97 (d, J=8.0 Hz, 1H), 3.20 (d, J=8.1 Hz, 1H), 2.89-2.75 (m, 2H), 2.48-2.39 (m, 1H), 2.17-2.03 (m, 2H), 2.01-1.88 (m, 2H), 1.64-1.48 (m, 3H), 1.48-1.38 (m, 2H), 1.06 (s, 3H), 0.95 (s, 9H), 0.91-0.81 (m, 2H), 0.58 (dd, J=12.7, 4.1 Hz, 1H), 0.16 (s, 6H); $^{13}$C NMR (150 MHz, CDCl$_3$) δ153.2, 144.5, 142.3, 137.8, 134.3, 133.0, 132.8, 126.0, 125.7, 125.5, 119.8, 117.0, 55.9, 49.0, 45.8, 43.4, 39.3, 35.4, 29.7 (2 C), 28.4, 28.3, 26.4, 25.8, 25.7 (3 C), 21.5, 18.1, −4.4 (2 C); HRMS (ESI-MS) calcd for C$_{33}$H$_{43}$NOSiH$^+$[M+H$^+$]: 498.3187, found 498.3195.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A compound whose structure corresponds to Formula XII,

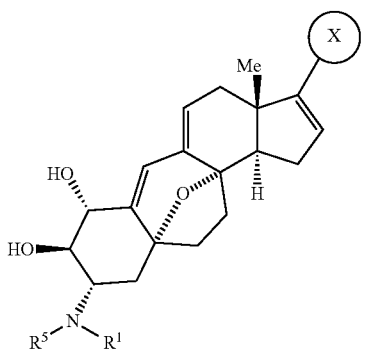

wherein
R$^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur;
R$^5$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur; and
the circled X is a heterocyclic substituent that contains 4 to about 15 carbon atoms, contains one to three saturated or unsaturated rings and up to three atoms per ring that are other than carbon and can be oxygen, nitrogen or sulfur.

2. The compound according to claim 1, wherein the circled X group is aromatic.

3. The compound according to claim 2, whose structure corresponds to the formula

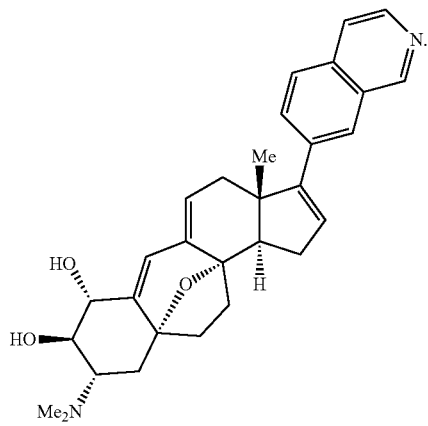 [SMILES: CN(C)[C@H]1C[C@@]23CC[C@@]4(O2)C(=CC[C@]2(C)C(c5ccc6ccncc6c5)=CC[C@H]24)C=C3[C@@H](O)[C@@H]1O]

4. A method of preparing a compound whose structure corresponds to Formula XII that comprises
1) reacting a compound whose structure corresponds to Formula XI

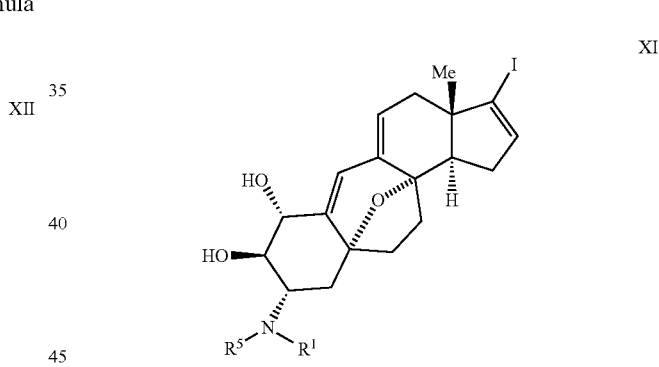

wherein
R$^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur; and
R$^5$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur, with a trimethyltin derivative of a circled X moiety that is a heterocyclic substituent that contains 4 to about 15 carbon atoms, contains one to three saturated or unsaturated rings and up to three atoms per ring that are other than carbon and can be oxygen, nitrogen or sulfur to form a compound whose structure corresponds to Formula XII,

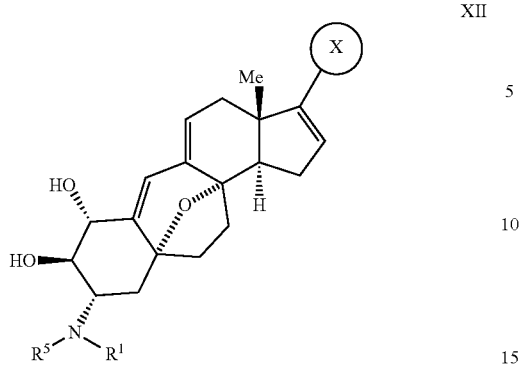
wherein R¹ and R⁵ are as defined for a compound whose structure corresponds to Formula XI.
5. The method according to claim 4, wherein R¹ and R⁵ are both methyl.
6. The method according to claim 4, wherein the circled X is 7-isoquinoline.
7. The method according to claim 4, wherein the circled X is aromatic.
* * * * *